United States Patent
Koga et al.

(10) Patent No.: US 7,906,508 B2
(45) Date of Patent: Mar. 15, 2011

(54) 3,4-DIHYDROBENZOXAZINE COMPOUNDS AND INHIBITORS OF VANILLOID RECEPTOR SUBTYPE 1 (VR1) ACTIVITY

(75) Inventors: Yoshihisa Koga, Takatsuki (JP); Shinji Yata, Takatsuki (JP); Takayuki Yamasaki, Takatsuki (JP); Tatsuya Matsumoto, Takatsuki (JP); Masahiro Sakata, Takatsuki (JP); Wataru Kondo, Takatsuki (JP); Yoshikazu Hori, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 748 days.

(21) Appl. No.: 11/616,962

(22) Filed: Dec. 28, 2006

(65) Prior Publication Data

US 2007/0149517 A1  Jun. 28, 2007

Related U.S. Application Data

(60) Provisional application No. 60/756,296, filed on Jan. 5, 2006.

(30) Foreign Application Priority Data

Dec. 28, 2005  (JP) ................. 2005-377754

(51) Int. Cl.
C07D 413/04 (2006.01)
C07D 413/14 (2006.01)
A61K 31/538 (2006.01)

(52) U.S. Cl. .................... 514/230.5; 544/105
(58) Field of Classification Search .............. 544/105; 514/230.5
See application file for complete search history.

(56) References Cited

U.S. PATENT DOCUMENTS

| | | | |
|---|---|---|---|
| 1,893,091 A | 1/1933 | Laska et al. |
| 3,678,094 A | 7/1972 | Shen et al. |
| 3,773,936 A | 11/1973 | Shen et al. |
| 4,640,916 A | 2/1987 | Meguro et al. |
| 5,712,298 A | 1/1998 | Amschler |
| 5,998,400 A | 12/1999 | Brieaddy et al. |
| 6,239,267 B1 | 5/2001 | Duckworth et al. |
| 6,268,387 B1 | 7/2001 | Connor et al. |
| 6,495,555 B1 | 12/2002 | Kennis et al. |
| 6,528,528 B2 | 3/2003 | Connor et al. |
| 6,624,184 B1 | 9/2003 | Gu et al. |
| 6,723,730 B2 | 4/2004 | Bakthavatchalam et al. |
| 6,933,311 B2 | 8/2005 | Lee et al. |
| 7,067,507 B2 | 6/2006 | Pulley et al. |
| 7,067,553 B2 | 6/2006 | Suh et al. |
| 7,074,805 B2 | 7/2006 | Lee et al. |
| 7,335,678 B2 | 2/2008 | Lee et al. |
| 2001/0047090 A1 | 11/2001 | Duckworth et al. |
| 2003/0153596 A1 | 8/2003 | Suh et al. |
| 2003/0158188 A1 | 8/2003 | Lee et al. |
| 2003/0158198 A1 | 8/2003 | Lee et al. |
| 2003/0195201 A1 | 10/2003 | Bo et al. |
| 2003/0212140 A1 | 11/2003 | Suh et al. |
| 2003/0236280 A1 | 12/2003 | Codd et al. |
| 2004/0038969 A1 | 2/2004 | Doherty et al. |
| 2004/0044003 A1 | 3/2004 | Kyle et al. |
| 2004/0082562 A1 | 4/2004 | Gu et al. |
| 2004/0082780 A1 | 4/2004 | Doherty et al. |
| 2004/0102497 A1 | 5/2004 | Gu et al. |
| 2004/0122089 A1 | 6/2004 | Martin et al. |
| 2004/0138252 A1 | 7/2004 | Ikeda et al. |
| 2004/0142958 A1 | 7/2004 | Herzberg et al. |
| 2004/0157849 A1 | 8/2004 | Lee et al. |
| 2004/0176443 A1 | 9/2004 | Bakthavatchalam et al. |
| 2004/0209884 A1 | 10/2004 | Lee et al. |
| 2005/0004133 A1 | 1/2005 | Makings et al. |
| 2005/0107388 A1 | 5/2005 | Brown et al. |
| 2005/0158827 A1 | 7/2005 | Curtis |
| 2005/0165046 A1 | 7/2005 | Hulme et al. |
| 2005/0165049 A1 | 7/2005 | Hulme et al. |
| 2005/0176726 A1 | 8/2005 | Wang et al. |
| 2005/0182067 A1 | 8/2005 | Balan et al. |
| 2005/0227986 A1 | 10/2005 | Bo et al. |
| 2005/0267163 A1 | 12/2005 | Doherty et al. |

(Continued)

FOREIGN PATENT DOCUMENTS

CA  2 571 133 A1  1/2006

(Continued)

OTHER PUBLICATIONS

Bevan et al., *TINS*, 17(12): 509-512 (1994).
Birder et al., *Nature Neuroscience*, 5(9): 856-860 (2002).
Carlton et al, *Neuroscience Letters*, 310: 53-56 (2001).
Caterina et al., *Nature*, 389: 816-824 (1997).
Caterina et al., *Science*, 288: 306-313 (2000).
Chuang et al., *Nature*, 411: 957-962 (2001).

(Continued)

*Primary Examiner* — Kahsay T Habte
(74) *Attorney, Agent, or Firm* — Leydig, Voit & Mayer, Ltd.

(57) ABSTRACT

A 3,4-dihydrobenzoxazine compound of the present invention is represented by the following formula [1] (wherein X is a nitrogen atom or $CR^3$; $R^1$ is a hydrogen atom or a halogen atom; $R^2$ is a C1-6 alkoxy group which may be substituted with the same or different 1 to 5 substituents selected from a halogen atom and a hydroxyl group; and $R^3$ is a halogen atom. However, $R^1$ is a halogen atom when X is $CR^3$). This compound is effective in treating diseases to which the vanilloid receptor subtype 1 (VR1) activity is involved, such as pain, etc.

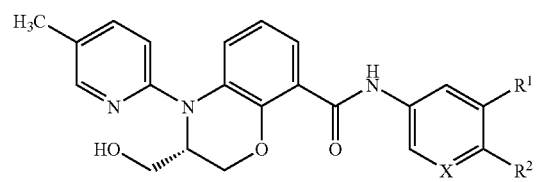

[1]

21 Claims, No Drawings

U.S. PATENT DOCUMENTS

| | | |
|---|---|---|
| 2005/0272777 A1 | 12/2005 | Doherty et al. |
| 2005/0272931 A1 | 12/2005 | Bo et al. |
| 2005/0277631 A1 | 12/2005 | Doherty et al. |
| 2005/0277646 A1 | 12/2005 | Doherty et al. |
| 2006/0030618 A1 | 2/2006 | Bo et al. |
| 2006/0035882 A1 | 2/2006 | Koga et al. |
| 2006/0035939 A1 | 2/2006 | Koga et al. |
| 2006/0100202 A1 | 5/2006 | Raimi et al. |
| 2006/0142333 A1 | 6/2006 | MacDonald et al. |
| 2007/0149517 A1 | 6/2007 | Koga et al. |
| 2008/0064687 A1 | 3/2008 | Suh et al. |
| 2008/0214524 A1 | 9/2008 | Lee et al. |
| 2009/0105298 A1 | 4/2009 | Ikeda et al. |

FOREIGN PATENT DOCUMENTS

| | | | |
|---|---|---|---|
| CN | | 1006382 B | 1/1990 |
| CN | | 1126468 A | 7/1996 |
| CN | | 1059674 C | 12/2000 |
| CN | | 1335845 A | 2/2002 |
| JP | | 57141456 A | 9/1982 |
| JP | | 09-059236 A | 3/1997 |
| JP | | 2001-526255 A | 12/2001 |
| JP | | 2004-506714 | 3/2003 |
| JP | | 2003-192673 A | 7/2003 |
| JP | | 2005-516951 | 6/2005 |
| JP | | 2005-518371 | 6/2005 |
| WO | WO 97/48697 | A1 | 12/1997 |
| WO | WO 99/32433 | A1 | 7/1999 |
| WO | WO 00/020421 | A2 | 4/2000 |
| WO | WO 00/26197 | A1 | 5/2000 |
| WO | WO 00/29577 | A1 | 5/2000 |
| WO | WO 00/32766 | A1 | 6/2000 |
| WO | WO 00-040580 | A1 | 7/2000 |
| WO | WO 00/63415 | A1 | 10/2000 |
| WO | WO 02/08221 | A2 | 1/2002 |
| WO | WO 02/16318 | A1 | 2/2002 |
| WO | WO 02/064545 | A1 | 8/2002 |
| WO | WO 02/074726 | A2 | 9/2002 |
| WO | WO 03/006019 | A1 | 1/2003 |
| WO | WO 03/049702 | A2 | 6/2003 |
| WO | WO 03/053945 | A2 | 7/2003 |
| WO | WO 03/066593 | A2 | 8/2003 |
| WO | WO 03/068749 | A1 | 8/2003 |
| WO | WO 03/070247 | A1 | 8/2003 |
| WO | WO 03/080578 | A1 | 10/2003 |
| WO | WO 03/097586 | A1 | 11/2003 |
| WO | WO 03/099284 | A1 | 12/2003 |
| WO | WO 2004/009552 | A1 | 1/2004 |
| WO | WO 2004/022002 | A2 | 3/2004 |
| WO | WO 2004-052846 | A | 6/2004 |
| WO | WO 2004/054582 | A1 | 7/2004 |
| WO | WO 2004/056394 | A1 | 7/2004 |
| WO | WO 2004-056774 | A | 7/2004 |
| WO | WO 2004/108133 | A1 | 12/2004 |
| WO | WO 2005/023807 | A2 | 3/2005 |
| WO | WO 2005/070885 | A1 | 8/2005 |
| WO | WO 2005/077938 | A1 | 8/2005 |
| WO | WO 2005/077944 | A1 | 8/2005 |
| WO | WO 2005/103018 | A1 | 11/2005 |
| WO | WO 2006/006741 | A1 | 1/2006 |

OTHER PUBLICATIONS

Davis et al., *Nature*, 405: 183-187 (2000).
Ikeda et al., *Life Sciences*, 69: 2911-2919 (2001).
Numazaki et al., *Biochemistry*, 75: 359-371 (2003).
Premkumar et al., *J. Physiol.*, 545(1): 107-117 (2002).
Purandare et al., *Tetrahedron Letters*, 43: 3903-3906 (2002).
Shu et al., *Neuroscience Letters*, 274: 159-162 (1999).
Sugiura et al., *J. Neurophysiol.*, 88: 544-548 (2002).
Szallasi et al., *Pharmacological Reviews*, 51(2): 159-211 (1999).
Tominaga et al., *PNAS*, 98(12): 6951-6956 (2001).
Yang et al., *J. Neurosci.*, 22(15): 6388-6393 (2002).
Yiangou et al., *The Lancet*, 357: 1338-1339 (2001).
Correll et al., *Expert Opinion on Therapeutic Patents*, 16(6): 783-95 (2006).
Planells-Cases et al., *Expert Opinion on Drug Discovery*, 2(8): 1053-63 (2007).
"Post-Operative Pain," http://www.painmd.com/types-of-pain/general-pain/postoperative-pain.html, accessed Jan. 4, 2010.
U.S. Appl. No. 11/181,235, Office Action dated Dec. 19, 2007.
U.S. Appl. No. 11/181,235, Reply to Office Action dated Jun. 13, 2008.
U.S. Appl. No. 11/181,235, Office Action dated Jun. 20, 2008.
U.S. Appl. No. 11/181,235, Reply to Office Action dated Sep. 9, 2008.
U.S. Appl. No. 11/181,235, Office Action dated Oct. 7, 2008.
U.S. Appl. No. 11/181,235, Reply to Office Action dated Jan. 7, 2009.
U.S. Appl. No. 11/183,265, Office Action dated Oct. 4, 2007.
U.S. Appl. No. 11/183,265, Reply to Office Action dated Nov. 2, 2007.
U.S. Appl. No. 11/183,265, Office Action dated Dec. 18, 2007.
U.S. Appl. No. 11/183,265, Reply to Office Action dated Apr. 9, 2008.
U.S. Appl. No. 11/183,265, Office Action dated Jul. 22, 2008.
U.S. Appl. No. 11/183,265, Office Action dated Sep. 29, 2008.
U.S. Appl. No. 11/183,265, Reply to Office Action dated Dec. 29, 2008.
U.S. Appl. No. 11/183,265, Office Action dated Apr. 1, 2009.
U.S. Appl. No. 11/183,265, Reply to Office Action dated Jul. 1, 2009.
U.S. Appl. No. 11/183,265, Advisory Action dated Aug. 4, 2009.
U.S. Appl. No. 11/183,265, Notice of Appeal dated Oct. 1, 2009.
U.S. Appl. No. 11/183,265, Pre-Appeal Brief Request for Review dated Oct. 1, 2009.
U.S. Appl. No. 11/183,265, Notice of Panel Decision dated Jan. 15, 2010.
U.S. Appl. No. 11/183,265, Office Action dated Jan. 28, 2010.
U.S. Appl. No. 11/183,265, Reply to Office Action dated Jun. 28, 2010.
U.S. Appl. No. 12/430,268, Office Action dated Mar. 30, 2010.
U.S. Appl. No. 12/430,268, Reply to Office Action dated Jun. 30, 2010.
Mashkovsky, M.D., *Medicaments*, vol. 1, p. 11 (2001), English Translation of RU Office Action.
U.S. Appl. No. 11/183,265, Office Action dated Sep. 17, 2010.
U.S. Appl. No. 12/430,268, Office Action dated Aug. 19, 2010.

3,4-DIHYDROBENZOXAZINE COMPOUNDS AND INHIBITORS OF VANILLOID RECEPTOR SUBTYPE 1 (VR1) ACTIVITY

TECHNICAL FIELD

The present invention relates to a novel 3,4-dihydrobenzoxazine compound having an inhibitory effect on vanilloid receptor subtype 1 (VR1) activity and a pharmaceutically acceptable salt thereof, a pharmaceutical composition comprising the compound or pharmaceutically acceptable salt thereof as an active ingredient, and a method for treating and/or preventing diseases to which the vanilloid receptor subtype 1 (VR1) activity is involved, such as pain, acute pain, chronic pain, neuropathic pain, rheumatoid arthritis pain, neuralgia, etc., particularly pain.

BACKGROUND ART

Capsaicin, which is the main ingredient of red pepper, is a pungency causing ingredient as well as a pain producing substance. It has been reported that many nociceptive nerves, particularly unmyelinated C fibers have capsaicin sensitivity and it is known that C fibers will selectively drop out when capsaicin is administered to an infant rodent. It has been also reported that there are many sites of action for capsaicin distributed in the skin, cornea, and oral mucosa, and the distribution thereof is also observed in the muscles, joints and internal organs, particularly in the cardiovascular system, respiratory system and bladder urinary tract system, and it is important for activation of sensory nerve. In addition, capsaicin sensitivity is also observed in the nerves of the preoptic area of the thalamus, and involvement in the regulation of body temperature is presumed. Depolarization by inflow of $Na^+$ and $Ca^{2+}$ by capsaicin administration is observed in the nociceptive nerves and discharge of glutamic acid and neuropeptides (mainly Substance P and calcitonin gene-related peptide) from the center side end of the primary afferent fiber of the spinal dorsal horn is resulted. Now that specific binding activity of resiniferatoxin (RTX) which brings about similar effects to that of capsaicin has been observed, and that capsazepine has been revealed as a competitive inhibitor, liposoluble capsaicin is considered to act on receptor protein (see Szallasi A, Blumberg P M. (1999) Pharmacol. Rev. 51, 159-212 (Non-Patent Document 1)).

The capsaicin receptor gene was cloned in 1997 (see, for example, Caterina M J, Schumacher M A Tominaga M, Posen T A, Levine J D, Julius D. (1997) Nature 389, 816-824 (Non-Patent Document 2)). It was presumed from its amino acid sequence that it was an ion channel having a six-transmembrane domain. Since capsaicin has a vanillyl group in the structure, it is generically referred to as vanilloids along with its analogs such as RTX, and the cloned receptor was named vanilloid receptor subtype 1 (hereinafter referred to as VR 1; This VR1 may be also referred to as TRPV1 (transient receptor potential vanilloid 1)). Then, electrophysiological functional analysis using the patch clamping method has been performed by making oocytes of *Xenopus laevis* and human derived cultured cells to express VR1, and it has been revealed that VR1 is directly activated by capsaicin, without mediated by an intracellular second messenger (see, for example, Caterina M J, Schumacher M A Tominaga M, Posen T A, Levine J D, Julius D. (1997) Nature 389, 816-824 (Non-Patent Document 2)), and that VR1 is a non-selective cation ion channel having high $Ca^{2+}$ permeability with an outward rectification property (see, for example, Premkumar L S, Agarwal S, Steffen D. (2002) J. Physiol. 545, 107-117 (Non-Patent Document 3)).

Although capsaicin is a pain causing substance, it is used as an analgesic agent to mitigate pain in diabetic neuropathy or rheumatic neurosis (see, for example, Szallasi A, Blumberg P M. (1999) Pharmacol. Rev. 51, 159-212 (Non-Patent Document 1)). It is understood that such mitigation is resulted from a phenomenon that the sensory nerve end exposed to capsaicin stops answering to pain stimulus that is, desensitization. Although it is considered that the desensitization mechanism of VR1 involves $Ca^{2+}$-mediated regulation, regulation depending on potential, activity control of VR1 by phosphorylation and dephosphorylation, etc., many points remain unclear.

As well as capsaicin, heat and acid also cause pain and it is known that the capsaicin sensitive nociceptive nerves respond to two or more types of stimulation. It was found that VR1 was directly activated by not only capsaicin but heat stimulation of 43° C. or more (see, for example, Yang D, Gereau R W 4th. (2002) J. Neurosci. 22, 6388-6393 (Non-Patent Document 4)). The temperature of 43° C. is mostly in agreement with the temperature threshold which causes a pain in humans and animals, suggesting that VR1 participates in nociceptive heat stimulation receptance.

Acidification occurs in an organ in the case of inflammation or ischemia and it is known to cause or enhance pain (see, for example, Bevan S, Geppetti P. (1994) Trends Neurosci. 17, 509-512 (Non-Patent Document 5)). It has turned out that when the pH outside cells is reduced within the limits of the acidification which takes place in the case of an organ lesion, VR1 can be directly activated by the acidification (proton) alone, and it is surmised that VR1 is the actual molecule which receives stimulation by acidification in an organ which takes place in the case of inflammation or ischemia (see, for example, Yang D, Gereau R W 4th. (2002) J. Neurosci. 22, 6388-6393 (Non-Patent Document 4)).

Immunohistological analysis using a specific antibody has confirmed that the number of unmyelinated C fibers expressing VR1 increases in an inflamed region as compared in a normal region (see, for example, Carlton S M, Coggeshall R E. (2001) Neurosci. Lett. 310, 53-56 (Non-Patent Document 6)). The enhancement of VR1 expression in submucosal plexus has been actually observed in human inflammatory bowel disease (see, for example, Yiangou Y, Facer P, Dyer N H, Chan C L, Knowles C, Williams N S, Anand P. (2001) Lancet 357, 1338-1339 (Non-Patent Document 7)). Such an increase in the amount of VR1 expression causes peripheral sensitization in an inflamed organ and presumably contributes to duration of inflammatory hyperalgesia.

It has been also reported that extracellular ATP, bradykinin and a neuro growth factor which are inflammation related substances increase VR1 activity (see, for example, Tominaga M, Wada M, Masu M. (2001) Proc. Natl. Acad. Sci. USA 98, 6951-6956 (Non-Patent Document 8); Shu X, Mendell L M. (1999) Neurosci. Lett. 274, 159-162 (Non-Patent Document 9); Chuang H H, Prescott E D, Kong H, Shields S, Jordt S E, Basbaum A I, Chao, M V, Julius D. (2001) Nature 411, 957-962 (Non-Patent Document 10); and Sugiura T, Tominaga M, Katsuya H, Mizumura K. (2002) J. Neurophysiol. 88, 544-548 (Non-Patent Document 11)) and it is said to be a fact without doubt that VR1 involves in pain and hypersensitivity of pain including those caused by inflammation (see, for example, Numazaki M, Tominaga M (2003) Biochemistry 75, 359-371 (Non-Patent Document 12)).

The sensory nerve cells in a VR1-deficient mouse responded to none of capsaicin, proton and heat stimulation.

It is also reported that in action analysis, VR1-deficient mouse does not show the pain reaction following capsaicin administration, and sensitivity to heat stimulation decreases and inflammatory hyperalgesia is not observed (see, for example, Caterina M J, Leffler A, Malmberg A B, Martin W J, Trafton J, Peterson-Zeitz K R, Koltzenburg M, Basbaum A I, Julius D. (2000) Science 288, 306-313 (Non-Patent Document 13) and Davis L B, Gray J, Gunthorpe M J et al. (2000) Nature 405, 183-187 (Non-Patent Document 14)). Thus, it has been confirmed also on an individual level from the analysis of VR1-deficient mouse that VR1 functions as a wide range pain stimulation receptor.

Moreover, as for the relation between vanilloid receptor subtype 1 (VR1) and a disease, it has been reported already that a substance which inhibits VR1 activity is useful as a therapeutical agent of various diseases.

Particularly with regard to a therapeutical agent of pain, there is a report that capsazepine which is known as a VR1 antagonist has exhibited a significant analgesic effect in an animal model (see, for example, Ikeda Y, Ueno A, Naraba H, Oh-ishi S, (2001) Life Science 69, 2911-2919 (Non-Patent Document 15)), and use is expected as a new therapeutical agent of pain having an inhibitory effect of VR1 activity.

It has been confirmed with regard to bladder hyperstrain type frequent urination and urinary incontinence that the bladder contraction function of VR1-deficient mouse decreases and there is a report that a compound having a capsaicin-like pharmacological mechanism or a compound having an inhibitory action on VR1, i.e., a compound inhibiting vanilloid receptor subtype 1 (VR1) activity is useful for improving bladder function, for example, as a therapeutical agent of frequent urination, urinary incontinence, etc (see, for example, (2002) Nat. Neurosci. 5, 856-860 (Non-Patent Document 16)).

In addition, another reference reports that a substance having an inhibitory effect to the vanilloid receptor subtype 1 (VR1), particularly antagonist of VR1 receptor is useful for preventing and treating diseases related to VR1 activity, particularly urgent urinary incontinence, overactive bladder, chronic pain, neuropathic pain, postoperative pain, rheumatoid arthritis pain, neuralgia, neuropathy, hyperalgesia, nerve damage, ischemic symptom, neurodegenerative, cerebral apoplexy, incontinence, and inflammatory disease (see, for example, JP 2003-192673 (Patent Document 1)).

Furthermore, it is also known that diseases relevant to the vanilloid receptor activity may include pain, acute pain, chronic pain, neuropathic pain, postoperative pain, migraine, joint pain, neuropathy, nerve damage, diabetic nervous disease, neurodegenerative disease, neurogenic skin disorder, cerebral apoplexy, bladder hypersensitivity, irritable bowel syndrome, abnormalities in respiratory organs such as asthma and chronic obstructive pulmonary disease, stimulation of skin, eye or mucosa, fever, stomach or duodenal ulcer, inflammatory bowel disease, inflammatory disease, etc (see, for example, JP 2004-506714 T2 (Patent Document 2)).

Accordingly, it can be said that substances having vanilloid receptor subtype 1 (VR1) antagonistic activity is useful as a therapeutic agent for conditions in which C fibers participates, for example, not to mention pruritus, allergic and allergic rhinitis, overactive bladder type frequent urination and urinary incontinence, apoplexy, irritable bowel syndrome, respiratory ailment such as asthma and chronic obstructive pulmonary disease, dermatitis, mucositis, stomach and duodenal ulcer, inflammatory bowel disease, etc. but also pain, acute pain, chronic pain, neuropathic pain, postoperative pain, migraine, joint pain, neuropathy, nerve damage, diabetic nervous disease, neurodegenerative disease, rheumatoid arthritis pain, neuralgia, neuropathy, hyperalgesia, neurogenic skin disorder, apoplexy, overweight, urgent urinary incontinence, ischemic symptom and an inflammatory disease, etc.

Next, compounds considered to relatively resemble the known vanilloid receptor subtype 1 (VR1) antagonist and the compound of present invention are described.

The amide-type compounds represented by the following general formula [A], [B] and [C] are disclosed in WO03/068749 as compounds exhibiting antagonism to VR1 (Patent Document 3).

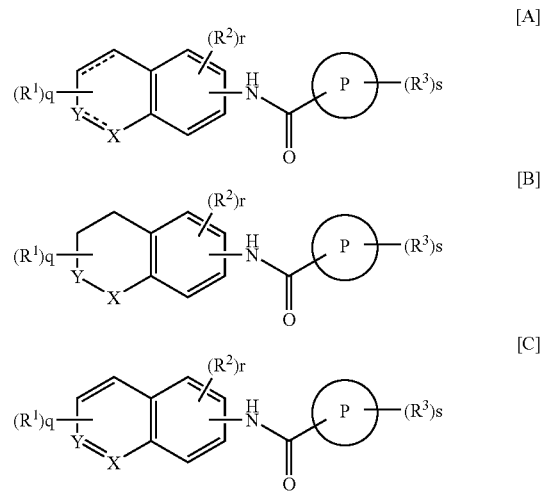

The urea-type compound represented by the following general formula [D] is disclosed in WO03/080578 as a compound exhibiting antagonism to VR1 (Patent Document 4).

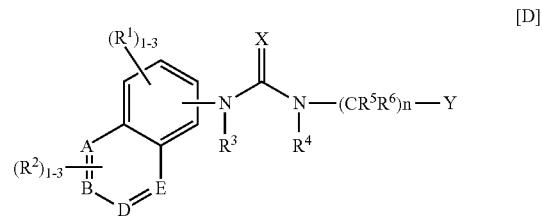

Quinuclidine-3'-yl 1-phenyl-1,2,3,4-tetrahydroisoquinoline-2-carboxylate is disclosed as a compound exhibiting an inhibitory effect against capsaicin-induced extravasation of a plasma protein in the bladder is disclosed in WO03/006019 (Patent Document 5).

The urea-type compound represented by the following general formula [E] is disclosed in WO03/053945 as a compound exhibiting antagonism to VR1 (Patent Document 6).

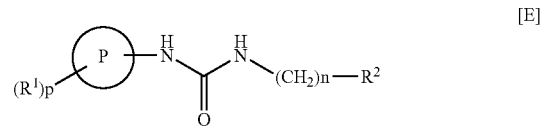

The compound represented by the following general formula [F] is disclosed as a compound in WO03/099284 as a compound exhibiting binding activity to VR1 (Patent Document 7).

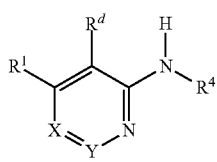

However, these compounds are different from the compound of the present invention in the structure, and there can be found no description which suggests the compound of the present invention.

For reference, the present inventors have previously made the patent application for a VR1 inhibitor represented by the following formula (PCT/JP2005/013446 (Patent Document 8)):

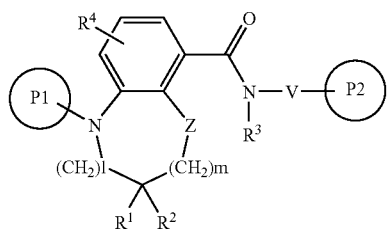

[Non-Patent Document 1] Szallasi A, Blumberg P M. (1999) Pharmacol. Rev. 51, 159-212
[Non-Patent Document 2] Caterina M J, Schumacher M A Tominaga M, Posen T A, Levine J D, Julius D. (1997) Nature 389, 816-824
[Non-Patent Document 3] Premkumar L S, Agarwal S, Steffen D. (2002) J. Physiol. 545, 107-117
[Non-Patent Document 4] Yang D, Gereau R W 4th. (2002) J. Neurosci. 22, 6388-6393
[Non-Patent Document 5] Bevan S, Geppetti P. (1994) Trends Neurosci. 17, 509-512
[Non-Patent Document 6] Carlton S M, Coggeshall R E. (2001) Neurosci. Lett. 310, 53-56
[Non-Patent Document 7] Yiangou Y, Facer P, Dyer N H, Chan C L, Knowles C, Williams N S, Anand P. (2001) Lancet 357, 1338-1339
[Non-Patent Document 8] Tominaga M, Wada M, Masu M. (2001) Proc. Natl. Acad. Sci. USA 98, 6951-6956
[Non-Patent Document 9] Shu X, Mendell L M. (1999) Neurosci. Lett. 274, 159-162
[Non-Patent Document 10] Chuang H H, Prescott E D, Kong H, Shields S, Jordt S E, Basbaum A I, Chao, M V, Julius D. (2001) Nature 411, 957-962
[Non-Patent Document 11] Sugiura T, Tominaga M, Katsuya H, Mizumura K. (2002) J. Neurophysiol. 88, 544-548
[Non-Patent Document 12] Numazaki M, Tominaga M (2003) Biochemistry 75, 359-371
[Non-Patent Document 13] Caterina M J, Leffler A, Malmberg A B, Martin W J, Trafton J, Peterson-Zeitz K R, Koltzenburg M, Basbaum A I, Julius D. (2000) Science 288, 306-313
[Non-Patent Document 14] Davis L B, Gray J, Gunthorpe M J et al. (2000) Nature 405, 183-187
[Non-Patent Document 15] Ikeda Y, Ueno A, Naraba H, Ohishi S, (2001) Life Science 69, 2911-2919
[Non-Patent Document 16] (2002) Nat. Neurosci. 5, 856-860
[Patent Document 1] JP 2003-192673 A2
[Patent Document 2] JP 2004-506714 T2
[Patent Document 3] WO03/068749
[Patent Document 4] WO03/080578
[Patent Document 5] WO03/006019
[Patent Document 6] WO03/053945
[Patent Document 7] WO03/099284
[Patent Document 8] PCT/JP2005/013446

DISCLOSURE OF THE INVENTION

Problems to be Solved by the Invention

As an analgesic agent, narcotic analgesics (morphine etc.), nonnarcotic analgesics (NSAID (nonsteroidal anti-inflammatory drug)), etc. are mainly used now. However, use of narcotic analgesics is severely restricted due to development of resistance/dependency and other serious side effects. It is known well other that an upper gastrointestinal tract disorder and a liver disorder frequently occur during long-term administration of nonnarcotic analgesics, and analgesic agent with a few side effects with higher analgesic effect is eagerly desired. Furthermore, as for diabetes-induced neuropathic pain, postherpetic neuralgia, and neuropathic pain such as trigeminal neuralgia, no effective analgesic agent has been found yet and development of an effective analgesic agent thereof is also expected.

Capsaicin-like compounds which act on VR1 are considered to develop the analgesic effect based on a pharmacological mechanism completely different from those of existing analgesic agents (block of capsaicin-sensitive nerves), and the efficacy is greatly expected as a therapeutic agent for neuropathic pain and the pain which originates in various conditions such as rheumatic arthritis for which the existing analgesic agents are not effective.

The fact that the final target of various inflammation related substances is VR1 suggests possibility that an agent which acts on VR1 is effective for various inflammatory pains and interstitial cystitis and its efficacy is greatly expected as an analgesic agent which replaces the existing analgesic agents.

Therefore, the purpose of the present invention is to provide a new analgesic agent based on the pharmacological mechanism completely different from those of existing analgesic agents (block of capsaicin-sensitive nerves), i.e., VR1 activity inhibitor and to provide a novel compound for the same.

More specifically, the purpose of the present invention is to provide a VR1 activity inhibitor excellent in not only inhibitory activity on VR1 but also absorbability and sustainability which is more likely to be practically used.

Another purpose of the present invention is to provide a method for treating and/or preventing diseases to which the vanilloid receptor subtype 1 (VR1) activity is involved, such as pain, acute pain, chronic pain, neuropathic pain, rheumatoid arthritis pain, neuralgia, etc., particularly pain.

Means for Solving the Problems

As a result of intensive study for developing an analgesic agent based on new action mechanism which will replace conventional analgesic agents such as nonnarcotic analgesics, pyrazolone analgesics, non-pyrazolone analgesics and NSAIDs, the present inventors have found out a 3,4-dihydrobenzoxazine compound which has excellent inhibitory activity on VR1 action and has more excellent absorbability and more excellent sustainability, and completed the present invention. The present invention is described in more detail below.

1. A 3,4-dihydrobenzoxazine compound represented by the following general formula [1] or a pharmaceutically acceptable salt thereof:

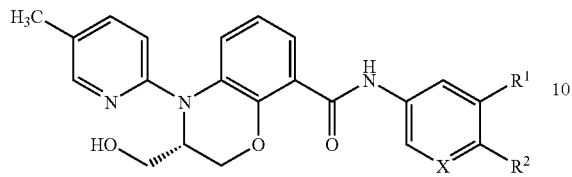

[1]

[wherein X is
(1) a nitrogen atom or
(2) CR$^3$;
R$^1$ is
(1) a hydrogen atom or
(2) a halogen atom;
R$^2$ is a C1-6 alkoxy group which may be substituted with the same or different 1 to 5 substituents selected from the following group:
(1) a halogen atom and
(2) a hydroxyl group; and
R$^3$ is a halogen atom (however, R$^1$ is a halogen atom when X is CR$^3$)].

2. The 3,4-dihydrobenzoxazine compound according to above 1 selected from the following group or a pharmaceutically acceptable salt thereof:
1) (S)-4-(5-picolin-2-yl)-3-hydroxymethyl-N-(4-tert-butoxy-3,5-difluorophenyl)-3,4-dihydro-2H-benzo[1,4]oxazine-8-carboxamide,
2) (S)-4-(5-picolin-2-yl)-3-hydroxymethyl-N-(3,5-difluoro-4-isopropoxyphenyl)-3,4-dihydro-2H-benzo[1,4]oxazine-8-carboxamide,
3) (S)-4-(5-picolin-2-yl)-3-hydroxymethyl-N-(3,5-difluoro-4-ethoxyphenyl)-3,4-dihydro-2H-benzo[1,4]oxazine-8-carboxamide,
4) (S)-4-(5-picolin-2-yl)-3-hydroxymethyl-N-[2-(2,2-dimethylpropyloxy)pyridin-5-yl]-3,4-dihydro-2H-benzo[1,4]oxazine-8-carboxamide,
5) (S)-4-(5-picolin-2-yl)-3-hydroxymethyl-N-(2-tert-butoxypyridin-5-yl)-3,4-dihydro-2H-benzo[1,4]oxazine-8-carboxamide,
6) (S)-4-(5-picolin-2-yl)-3-hydroxymethyl-N-[2-(2,2,2-trifluoroethyloxy)pyridin-5-yl]-3,4-dihydro-2H-benzo[1,4]oxazine-8-carboxamide,
7) (S)-4-(5-picolin-2-yl)-3-hydroxymethyl-N-(2-isobutoxypyridin-5-yl)-3,4-dihydro-2H-benzo[1,4]oxazine-8-carboxamide,
8) (S)-4-(5-picolin-2-yl)-3-hydroxymethyl-N-[3,5-difluoro-4-(2,2,2-trifluoroethoxy)phenyl]-3,4-dihydro-2H-benzo[1,4]oxazine-8-carboxamide,
9) (S)-4-(5-picolin-2-yl)-3-hydroxymethyl-N-[3,5-difluoro-4-(2-hydroxy-2-methylpropyloxy)phenyl]-3,4-dihydro-2H-benzo[1,4]oxazine-8-carboxamide, and
10) (S)-4-(5-picolin-2-yl)-3-hydroxymethyl-N-[3,5-difluoro-4-(1,1-dimethyl-2-hydroxyethyloxy)phenyl]-3,4-dihydro-2H-benzo[1,4]oxazine-8-carboxamide.

3. A pharmaceutical composition comprising a 3,4-dihydrobenzoxazine compound or a pharmaceutically acceptable salt thereof according to above 1 or 2 and a pharmaceutically acceptable carrier.

4. A pharmaceutical composition comprising a 3,4-dihydrobenzoxazine compound or a pharmaceutically acceptable salt thereof according to above 1 or 2 and a pharmaceutically acceptable carrier for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence.

5. A pharmaceutical composition for treating and/or preventing pain comprising a 3,4-dihydrobenzoxazine compound or a pharmaceutically acceptable salt thereof according to above 1 or 2 and a pharmaceutically acceptable carrier.

6. The pharmaceutical composition according to above 5 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

7. An inhibitor of vanilloid receptor subtype 1 (VR1) activity comprising a 3,4-dihydrobenzoxazine compound or a pharmaceutically acceptable salt thereof according to above 1 or 2 and a pharmaceutically acceptable carrier.

8. A method for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence characterized in that the method comprises administering a pharmacologically effective amount of a 3,4-dihydrobenzoxazine compound or a pharmaceutically acceptable salt thereof according to above 1 or 2.

9. A method for treating and/or preventing pain characterized in that the method comprises administering a pharmacologically effective amount of a 3,4-dihydrobenzoxazine compound or a pharmaceutically acceptable salt thereof according to above 1 or 2.

10. The treating and/or preventing method according to above 9 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

11. A commercial package comprising a pharmaceutical composition according to any of above 3 to 6 and written instructions concerning said pharmaceutical composition stating that said composition can be used or should be used for treating and/or preventing a disease selected from pain, acute pain, chronic pain, neuropathic pain, rheumatoid arthritis pain, neuralgia, neuropathy, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence.

12. Use of a 3,4-dihydrobenzoxazine compound or a pharmaceutically acceptable salt thereof according to above 1 or 2 for the preparation of a pharmaceutical composition according to above 4 for treating and/or preventing a disease selected from pain, acute pain, chronic pain, neuropathic pain, rheumatoid arthritis pain, neuralgia, neuropathy, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence.

13. Use of a 3,4-dihydrobenzoxazine compound or a pharmaceutically acceptable salt thereof according to above 1 or 2 for the preparation of a pharmaceutical composition for treating and/or preventing pain according to above 5 or 6.

14. The use of a 3,4-dihydrobenzoxazine compound or a pharmaceutically acceptable salt thereof according to above 13 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

15. A drug comprising a combination of a pharmaceutical composition comprising a 3,4-dihydrobenzoxazine compound or a pharmaceutically acceptable salt thereof according to above 1 or 2 and a pharmaceutically acceptable carrier with one or more agents selected from the group which consists of an anti-virus agent, an antidepressant, an anticonvulsant, an antiarrhythmic, a local anesthetic, an anesthetic, an N-methyl-D-aspartate receptor antagonist, an adrenal cortical steroid, a nerve block, a nonsteroidal antiinflammatory analgesic, a narcotic, an antagonist analgesic, an $\alpha_2$-adrenaline receptor agonist, a medicine for external application, a calcium channel antagonist, a potassium channel opener, and an antipyretic agent.

16. Use of a 3,4-dihydrobenzoxazine compound or a pharmaceutically acceptable salt thereof according to above 1 or 2 for the preparation of a drug according to above 15.

17. A method for treating and/or preventing a disease selected from pain, acute pain, chronic pain, neuropathic pain, rheumatoid arthritis pain, neuralgia, neuropathy, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence characterized in that one or more agents selected from the group which consists of an anti-virus agent, an antidepressant, an anticonvulsant, an antiarrhythmic drug, a local anesthetic, an anesthetic drug, an N-methyl-D-aspartate receptor antagonist, adrenal cortical steroid, a nerve blocks a non-steroidal anti-inflammatory analgesic, narcotics, an antagonist analgesic, $\alpha_2$-adrenaline receptor agonist, a medicine for external application, a calcium channel antagonist, a potassium channel opener, and an antipyretic agent are used in combination with a pharmacologically effective amount of a 3,4-dihydrobenzoxazine compound or a pharmaceutically acceptable salt thereof according to above 1 or 2.

18. A method for treating and/or preventing pain characterized in that the method uses administration of a 3,4-dihydrobenzoxazine compound or a pharmaceutically acceptable salt thereof according to above 1 or 2 in combination with stimulation-produced analgesia selected from acupuncture, transcutaneous electroacupuncture stimulation therapy, transcutaneous electrical nerve stimulation therapy, silver spike point (SSP) therapy, peripheral nerve stimulation therapy, spinal cord electrical stimulation therapy, electroconvulsive therapy, laser therapy and low-frequency therapy.

19. A method for treating and/or preventing postoperative neuralgia characterized in that a 3,4-dihydrobenzoxazine compound or a pharmaceutically acceptable salt thereof according to above 1 or 2 is administered after performing a surgical operation selected from cicatrectomy, nerve freezing solidification, peripheral nerve excision, spinal cord dorsal root excision, sympathectomy, spinal cord dorsal root entry zone destruction, cordotomy, and frontal lobe excision.

Advantages of the Invention

The 3,4-dihydrobenzoxazine compound of the present invention effectively inhibits vanilloid receptor subtype 1 (VR1) activity, and therefore it is effective in the medical treatment and/or prevention of diseases such as pain, acute pain, chronic pain, neuropathic pain, rheumatoid arthritis pain, neuralgia, neuropathy, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, overactive bladder type frequent urination, and overactive bladder type urinary incontinence.

Particularly, it is effective as a therapeutic agent and preventive agent of diseases accompanied with pain condition such as pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy and neurodegenerative disease. In addition, effects by different mechanism from the conventional analgesics are also expected.

The 3,4-dihydrobenzoxazine compound of the present invention represented by the above-mentioned general formula [1] not only has an excellent inhibitory effect on VR1 activity but also resists oxidative metabolism and has excellent effects in regard to the sustainability of the inhibitory effect. The compound of the present invention further has properties such as an exceedingly high absorbability, and/or exceedingly high stability in gastric juice. Such effects could not be predicted even by those skilled in the art.

Therefore, the novel compound of the present invention is an excellent compound which is more likely to be practically used as a drug.

BEST MODE FOR CARRYING OUT THE INVENTION

The definition of each term used in this specification is as follows.

A "C1-6 alkyl group" represents a linear or branched alkyl group having 1 to 6 carbon atoms, preferably "a C1-4 alkyl group". A "C1-6 alkyl group" specifically includes a methyl group, an ethyl group, a propyl group, an isopropyl group, a butyl group, an isobutyl group, a sec-butyl group, a tert-butyl group, a pentyl group, an isopentyl group, a tert-pentyl group, a hexyl group, etc. A "C1-4 alkyl group" represents a linear or branched alkyl group having 1 to 4 carbon atoms, and specifically includes a methyl group, an ethyl group, a propyl group, an isopropyl group, a butyl group, an isobutyl group, a sec-butyl group, a tert-butyl, etc.

A "halogen atom" is a fluorine atom, a chlorine atom, a bromine atom or an iodine atom, and a fluorine atom and a chlorine atom are preferred, and a fluorine atom is particularly preferred.

A "C1-6 alkoxy group" is an alkoxy group in which the alkyl part thereof is a "C1-6 alkyl group" of the above-mentioned definition. Specifically, it includes a methoxy group, an ethoxy group, a propoxy group, an isopropoxy group, a butoxy group, an isobutoxy group, a sec-butoxy group, a tert-butyloxy group, a pentyloxy group, an isopentyloxy group, a 2-methylbutoxy group, a neopentyloxy group, a 1-ethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 2-ethylbutoxy group, etc.

A "C1-6 alkoxy group which may be substituted with 1 to 5 halogen atoms" represents in addition to the above-mentioned "C1-6 alkoxy group", a haloalkoxy group in which the "C1-6 alkyl group" constituting the C1-6 alkoxy group part is substituted with 1 to 5, preferably 1 to 3, more preferably 3 and the same or different halogen atoms, preferably the same 3 halogen atoms. Specifically, such a haloalkoxy group includes a fluoromethoxy group, a difluoromethoxy group, a trifluoromethoxy group, a bromomethoxy group, a chloromethoxy group, a dichloromethoxy group, a 2-chloroethoxy group, a 1,2-dichloroethoxy group, a 2,2-dichloroethoxy group, a trichloromethoxy group, a 2-fluoroethoxy group, a 2,2,2-trifluoroethoxy group, a 2,2,2-trichloroethoxy group, a 4-fluorobutoxy group, etc.

A "C1-6 alkoxy group which may be substituted with 1 to 5 hydroxyl groups" represents in addition to the above-mentioned "C1-6 alkoxy group", an alkoxy group in which the "C1-6 alkyl group" constituting the C1-6 alkoxy group part is substituted with 1 to 5, preferably 1 to 2, more preferably 1 hydroxyl group. Specifically, such an alkoxy group substituted with a hydroxyl group includes a hydroxymethoxy group, a 2-hydroxyethoxy group, a 1-hydroxyethoxy group, a 3-hydroxypropoxy group, a 4-hydroxybutoxy group, a 5-hydroxypentyloxy group, a 6-hydroxyhexyloxy group, a 2-hydroxy-2-methylpropyloxy group, a 1,1-dimethyl-2-hydroxyethyloxy group, etc.

In the general formula [1], preferable examples and particularly preferable examples of each symbol are as follows. However, the present invention is not limited thereto.

[Preferable $R^1$]

$R^1$ is a hydrogen atom or a halogen atom. The halogen atom here is preferably a fluorine atom or a chlorine atom, particularly preferably a fluorine atom.

However, $R^1$ is preferably a hydrogen atom when X is a nitrogen atom, and $R^1$ is a halogen atom, particularly preferably a fluorine atom when X is $CR^3$.

More preferably, both $R^3$ and $R^1$ are fluorine atoms. More specifically, $R^1$ is as follows:

$R_1$ is
 (1) a hydrogen atom or
 (2) a halogen atom,
preferably
 (1) a hydrogen atom or
 (2) a fluorine atom
 (however, $R^1$ is preferably
a fluorine atom
when X is $CR^3$).

[Preferable $R^2$]

$R^2$ is a C1-6 alkoxy group which may be substituted with the same or different 1 to 5 substituents selected from a halogen atom and a hydroxyl group, preferably a C1-6 alkoxy group which may be substituted with 1 to 3 halogen atoms or 1 to 3 hydroxyl groups.

The "C1-6 alkoxy group" here may be an alkoxy group in which the alkyl group part is linear or an alkoxy group in which the alkyl group part is branched.

A preferable "C1-6 alkoxy group" is a C2-5 alkoxy group which may be branched. Specifically, it includes an ethoxy group, an isopropoxy group, an isobutoxy group, a tert-butoxy group, a 2,2-dimethyl-propoxy group, etc.

A "C1-6 alkoxy group which may be substituted with 1 to 3 halogen atoms" represents in addition to the above-mentioned C1-6 alkoxy group, a C1-6 alkoxy group substituted with 1 to 3 halogen atoms. The C1-6 alkoxy group substituted with 1 to 3 halogen atoms represents a C1-6 alkoxy group substituted with the same or different 1 to 3 halogen atoms, preferably the same 1 to 3 halogen atoms, particularly preferably 1 to 3 fluorine atoms. Specifically, it includes a 2,2,2-trifluoro-ethoxy group, a 2,2,2-trichloro-ethoxy group, a 2,2,2-tribromo-ethoxy group, a 2,2,2-triiodo-ethoxy group, etc. A particularly preferable "C1-6 alkoxy group substituted with 1 to 3 fluorine atoms" is a C2-5 alkoxy group substituted with 1 to 3 fluorine atoms. Specifically, it includes a 2,2,2-trifluoro-ethoxy group, etc.

A "C1-6 alkoxy group which may be substituted with 1 to 3 hydroxyl groups" represents in addition to the above-mentioned C1-6 alkoxy group, a C1-6 alkoxy group substituted with 1 to 3 hydroxyl groups, preferably 1 hydroxyl group. The C1-6 alkoxy group substituted with 1 to 3 hydroxyl groups is preferably a C2-5 alkoxy group substituted with 1 hydroxyl group. Specifically, it includes a 2-hydroxy-2-methyl-propoxy group, a 2-hydroxy-1,1-dimethyl-ethoxy group, etc.

[Preferable $R^3$]

$R^3$ is a halogen atom. The halogen atom here is preferably a fluorine atom or a chlorine atom, particularly preferably a fluorine atom. Particularly preferably, both $R^3$ and $R^1$ are fluorine atoms.

[Preferable $R^1$ and $R^2$ when X is Nitrogen Atom]

When X is a nitrogen atom, preferably $R^1$ is a hydrogen atom and $R^2$ is a C1-6 alkoxy group which may be substituted with the same or different 1 to 3 halogen atoms.

Particularly preferably $R^1$ is a hydrogen atom and $R^2$ is a C1-6 alkoxy group which may be substituted with the same 3 halogen atoms. More preferably $R^1$ is a hydrogen atom and $R^2$ is a tert-butoxy group, an isobutoxy group, a 2,2,2-trifluoro-ethoxy group or a 2,2-dimethyl-propoxy group.

[Preferable $R^1$, $R^2$ and $R^3$ when X is $CR^3$]

When X is $CR^3$, preferable $R^1$ and $R^3$ are $R^1$ and $R^3$ which are the same or different halogen atoms, particularly preferably the same halogen atoms.

More preferably, both $R^3$ and $R^1$ are fluorine atoms.

When X is $CR^3$, preferable $R^2$ is a C2-5 alkoxy group such as an ethoxy group, an isopropoxy group, an isobutoxy group, a tert-butoxy group, a 2,2-dimethyl-propoxy group, etc.; a C1-6 alkoxy group substituted with 1 to 3 halogen atoms, preferably fluorine atoms, such as a 2,2,2-trifluoro-ethoxy group, a 2,2,2-trichloro-ethoxy group, a 2,2,2-tribromo-ethoxy group, a 2,2,2-triiodo-ethoxy group, etc.; or a C1-6 alkoxy group substituted with 1 or 2 hydroxyl groups, such as a 2-hydroxy-2-methyl-propoxy group, a 2-hydroxy-1,1-dimethyl-ethoxy group, etc.

More specifically, when X is $CR^3$, $R^1$ and $R^3$ are preferably the same or different halogen atoms, particularly preferably fluorine atoms and $R^2$ is preferably a C1-6 alkoxy group which may be substituted with the same or different 1 to 3 substituents selected from a fluorine atom and a hydroxyl group, more specifically an ethoxy group, a tert-butoxy group, an isopropoxy group, a 2,2,2-trifluoro-ethoxy group, a 2-hydroxy-2-methyl-propoxy group or a 2-hydroxy-1,1-dimethyl-ethoxy group.

A "pharmaceutically acceptable salt" in the present invention may be any kind of salt as long as it forms a salt with a compound represented by the above-mentioned general formula [1], and can be obtained by reacting it with, for example, an inorganic acid such as hydrochloric acid, sulfuric acid, phosphoric acid, or hydrobromic acid; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, p-toluenesulfonic acid, benzenesulfonic acid, or benzylsulfonic acid; or an amino acid such as lysine, arginine or alanine. A hydrated compound, hydrate and solvate of each compound are also included in the present invention.

In addition, various isomers exist for the compound represented by the above-mentioned general formula [1]. For example, E isomer and Z isomer exist as geometric isomers, and when an asymmetric carbon atom exists, enantiomers and diastereomers exist as stereoisomers based on these, and tautomers may exist. Therefore, all of these isomers and the mixtures thereof are included in the range of the present invention. In addition, the present invention also encompasses prodrug compounds of these compounds and metabolite compounds as equivalent compounds besides the compound represented by the above-mentioned general formula [1].

A "prodrug" is a derivative of the compound of the present invention having a group which may be decomposed chemically or metabolically and after administered to a living body, it goes through a chemical change to a compound which has an activity as a drug and exhibits original pharmacological effect, and complexes and salts not by a covalent bond are included.

A prodrug is used for improving absorption upon oral administration or targeting to a target site. Moieties to be modified for forming a prodrug include reactive functional groups such as a hydroxyl group and an amino group in the compound of the present invention. Specific examples of the modifying group for a hydroxyl group include an acetyl group, a propionyl group, an isobutyryl group, a pivaloyl group, a benzoyl group, a 4-methylbenzoyl group, a dimethylcarbamoyl group, a sulfo group, etc. Specific examples of the modifying group for an amino group include a hexylcarbamoyl group, a 3-methylthio-1-(acetylamino)propylcarbonyl group, a 1-sulfo-1-(3-ethoxy-4-hydroxyphenyl)methyl group, a methyl(5-methyl-2-oxo-1,3-dioxol-4-yl) group, etc.

A "pharmaceutical composition" encompasses a combination drug with another drugs, etc., besides the so-called "composition" which comprises an active ingredient as a drug and a combinational agent, etc. Needless to say, the pharmaceutical composition of the present invention may be used in combination with any kind of other drugs as long as it is permitted in the medical scene. Therefore, it can also be said that this pharmaceutical composition is a pharmaceutical composition for the combined use with other drugs.

A "pain" means every type of pain condition no matter what the condition is (for example, no matter whether it is a dull pain or a sharp pain, chronic or acute, etc.), no matter which disease causes the pain (for example, no matter whether the pain is resulted from rheumatism, or the pain resulted from cancer, etc.). Therefore, the "pain" as used herein encompasses, in addition to the so-called "pain," acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, and neurodegenerative disease.

An "inhibitor of vanilloid receptor subtype 1 (VR1) activity" means a substance which inhibits the function of the vanilloid receptor subtype 1 as an ion channel, and eliminates or attenuates the activity. Specifically, it includes vanilloid receptor subtype 1 antagonist, etc. The vanilloid receptor subtype 1 antagonist means a substance which inhibits the effect of the agonist which acts on the vanilloid receptor subtype 1, thereby inhibiting the function of the vanilloid receptor subtype 1 as an ion channel. The inhibitor of the present invention has not to compete with the agonist but may also inhibit the function as a VR1 ion channel. Specifically, agonists which act on the vanilloid receptor subtype 1 include capsaicin, capsaicin derivatives, acid stimulation (proton), heat stimulation, etc., the inhibitor of vanilloid receptor subtype 1 (VR1) activity may be a substance which inhibits the $Ca^{2+}$ inflow into the cell caused by agonist stimulation of capsaicin, acid stimulation (proton) or heat stimulation.

The pharmaceutical composition of the present invention can be administered to human as well as other mammals (mouse, rat, hamster, rabbit, cat, dog, cow, horse, sheep, monkey, etc.). Therefore, the pharmaceutical composition of the present invention is useful also as a drug for animal not to mention for human.

When the compound of the present invention is used as a pharmaceutical preparation, it can be mixed with a pharmacologically acceptable carrier usually known in itself, excipient, diluent, extender, disintegrating agent, stabilizer, preservative, buffer, emulsifier, flavor, colorant, sweetener, thickener, corrigent, dissolution auxiliary agent, and other additive agents, specifically water, plant oil, alcohol such as ethanol or benzyl alcohol, carbohydrates such as polyethylene glycol, glycerol triacetate, gelatin, lactose and starch, magnesium stearate, talc, lanolin, vaseline, etc. to prepare a drug in the form such as tablet, pill, powder, granule, suppository, injection agent, eye-drops, liquid medicine, capsule agent, troche, aerosol agent, elixir agent, suspension, emulsion and syrup for systemic or local administration by oral or parenteral route.

Although the dosage varies depending on age, weight, condition, therapeutical effect, administration methods, etc., it is usually administered at a dose in the range of 0.01 mg to 1 g per dose, 1 time to several times per day, to adults, in the form of an oral preparate or injection preparation such as an intravenous injection, etc.

"Preventing" is the so-called prevention, and means, for example, suppressing the onset of neuralgia or chronicity of neuralgia prophylactically. As for pain, specifically included is prophylactically suppressing the onset of acute postherpetic neuralgia, onset of postherpetic neuralgia, transition to postherpetic neuralgia from acute herpetic pain, chronicity of postherpetic neuralgia, onset of postoperative pain, chronicity of postoperative pain, onset of symptoms of cancer pain, chronicity of cancer pain, onset of symptoms of inflammatory pain, onset of interstitial cystitis, chronicity of inflammatory pain, onset of posttraumatic neuralgia or chronicity of posttraumatic neuralgia.

A "drug comprising a combination" means a drug characterized in that it is a formulation containing a pharmaceutical composition comprising the compound [1] or pharmaceutically acceptable salt thereof of the present invention and a pharmaceutical composition or an agent to be combined with the composition of the present invention, a drug characterized in that it is a kit comprising a pharmaceutical composition comprising the compound [1] or pharmaceutically acceptable salt thereof of the present invention and a pharmaceutical composition or an agent to be combined with the composition of the present invention, a drug characterized in that a pharmaceutical composition comprising the compound [1] or pharmaceutically acceptable salt thereof of the present invention and a pharmaceutical composition or an agent to be combined with the composition of the present invention are administered via the same or different administration routes, respectively, etc.

The compound and pharmaceutical composition of the present invention can be used in combination with one or more other agents following a general method currently performed in the usual medical site. When used in combination, the drug to be used with may be administered simultaneously or separately with a time lag. Although there are various compounds which can be used in combination with the compound of the present invention, particularly preferred are an anti-virus agent, an antidepressant, an anticonvulsant, an anti-arrhythmic drug, a local anesthetic, an anesthetic drug, a N-methyl-D-aspartate receptor antagonist, adrenal cortical steroid, a nerve block, a nonsteroidal antiinflammatory analgesic, narcotics, an antagonist analgesic, an $\alpha_2$-adrenaline receptor agonist, a stimulation analgesic method, drugs for external application, a calcium channel antagonist, a potassium channel opener, and an antipyretic agent.

The anti-virus agent specifically includes vidarabine, acyclovir, ganciclovir, zidovudine, didanosine, amantadine, and idoxuridine, interferon, etc.

The antidepressant specifically includes amitriptyline, imipramine, clomipramine, trimipramine, lofepramine, dosulepin, desipramine, amoxapine, nortriptyline, fluoxetine, fluvoxamine, maprotiline, mianserin, setiptiline, trazodone, etc.

The anticonvulsant specifically includes gabapentin, pregabalin, phenobarbital, primidone, phenyloin, mephenyloin, nirvanol, ethotoin, trimethadione, ethosuximide, acetylpheneturide, carbamazepine, zonisamide, acetazolamide, diazepam, clonazepam, nitrazepam, diphenylhydantoin, valproic acid, baclofen, etc.

The antiarrhythmic drug specifically includes quinidine, disopyramide, procainamide, ajmaline, prajmalium, cibenzoline, lidocaine, mexiletine, aprindine, tonicaid, phenyloin, flecainide, pilcicainide, propafenone, propranolol, amiodarone, verapamil, bepridil, etc.

The local anesthetic specifically includes lidocaine, mexiletine, cocaine, procaine, bupivacaine, mepivacaine, prilocaine, tetracaine, dibucaine, ethyl aminobenzoate, etc.

The anesthetic drug specifically includes benzodiazepine, diazepam, midazolam, thiopental, thiamylal, propofol, baclofen, droperidol, sufentanil, etc. are mentioned. The N-methyl-D-aspartate receptor antagonist specifically includes ketamine, dextromethorphan, memantine, amantadine, etc. are included.

The adrenal cortical steroid specifically includes cortisol, cortisone, prednisolone, triamcinolone, dexamethasone, betamethasone, paramethasone, fluocinolone acetonide, fluocinonide, beclomethasone, fludrocortisone, etc.

The nerve block specifically includes stellate ganglion block, epidural ganglion block, brachial plexus ganglion block, nerve root block, thoracic/lumbar sympathetic ganglion, trigger point block, subarachnoid ganglion block, trigeminal nerve block, sympathetic nerve block, local infiltration block, peripheral nerve block, etc.

The nonsteroidal antiinflammatory analgesic specifically includes celecoxib, rofecoxib, etodolac, meloxicam, nimesulid, sodium diclofenac, mefenamic acid, zaltoprofen, sodium loxoprofen, sulindac, nabumetone, diflunisal, piroxicam, ibuprofen, naproxen, fenoprofen, acetylsalicylic acid, tolmetin, indomethacin, flurbiprofen, oxaprozin, ketoprofen, mofezolac, acetaminophen, ketorolac, zomepirac, nitroaspirin, tiaprofen, ampiroxicam, tiaramide, epirizole, etc.

The narcotics specifically include morphine, fentanyl, oxycodone, methadon, codeine, cocaine, pethidine, opium, ipecac, etc.

The antagonist analgesic specifically includes pentagyn, buprenorphine, nalorphine, cyclazocine, butorphanol, etc.

The $\alpha_2$-adrenaline receptor agonist specifically includes clonidine, dexmedetomidine, tizanidine, guanfacine, guanabenz, etc.

The medicine for external application specifically includes capsaicin cream etc.

The antipyretic agent specifically includes sodium diclofenac, mefenamic acid, sodium loxoprofen, ibuprofen, acetylsalicylic acid, indomethacin, acetaminophen, etc.

The stimulation analgesic method specifically includes acupuncture, a percutaneous electricity needle stimulation therapy, a percutaneous electricity nerve stimulation therapy, a silver spike point (SSP) treatment, a peripheral nerve stimulus, a spine electricity stimulus, an electric spasm treatment, laser surgery, a low-frequency therapy, etc.

In addition, the compound of the present invention can be used following the general method usually performed in the art by administration after performing a surgical operation to prevent or treat pain. Although various surgical operations can be performed in combination with the compound of the present invention, cicatrectomy, nerve freezing, peripheral nerve excision, spinal dorsal root excision, sympathectomy, spinal cord dorsal root entry zone destruction, cordotomy, and frontal lobe excision are particularly preferable.

Although application of the compound of the present invention has been described mainly as a use for preventing or treating pain, the compound of the present invention can be applied to the conditions in which C fibers participates, for example, pruritus, allergic and allergic rhinitis, overactive bladder type frequent urination and urinary incontinence, apoplexy, irritable bowel syndrome, respiratory ailment such as asthma and a chronic obstructive pulmonary disease, dermatitis, mucositis, stomach and duodenal ulcer, inflammatory bowel disease, etc.

Next, a preparation method of the compound of the present invention represented by the general formula [1] is described specifically but, needless to say, the present invention is not limited to these preparation methods.

Therefore, the compound of the present invention may be synthesized according to the following preparation methods A or B, but it can be prepared according to the below-mentioned examples, or referring to these processes. In preparation of the compound of the present invention, the order of reaction operation can be changed suitably. It can be performed starting from the reaction step or substitution part considered to be rational. For example, the compound (X) may be introduced before the compound (II) is introduced, and this order may be reversed. As for the formation of 3,4-dihydro enzoxazine, a closed ring reaction may be performed to form this hetero ring before introducing the compound (II) and/or compound (X) or alternatively, a closed ring reaction may be performed to form this hetero ring after introducing the compound (II) and/or compound (X). Protection and deprotection may be suitably conducted when there is a reactant functional group. In order to enhance development of the reaction, reagents other than those illustrated can be used suitably.

The following production process flow is an example of the typical preparation method, but preparation of the compound of the present invention is not particularly limited to the following method. Each compound obtained at each step can be isolated and purified by a usual method, but depending on the case the compound can be used in the next step without being isolated and purified.

1. Preparation Method A;

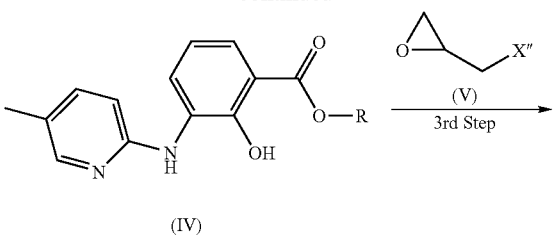

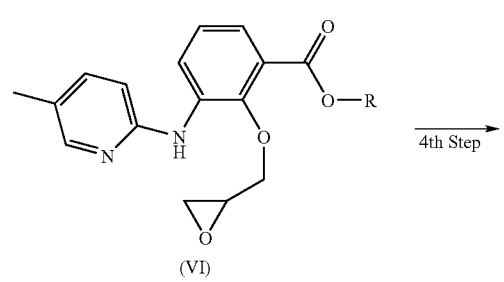

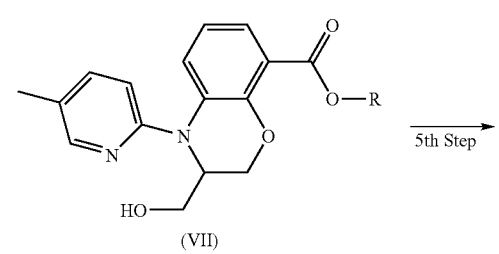

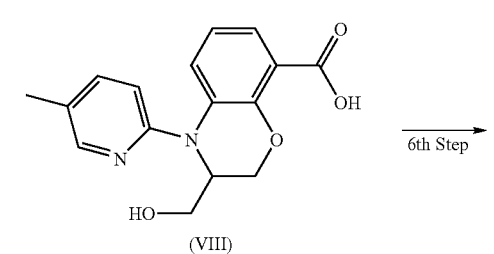

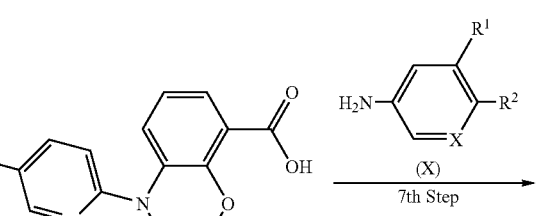

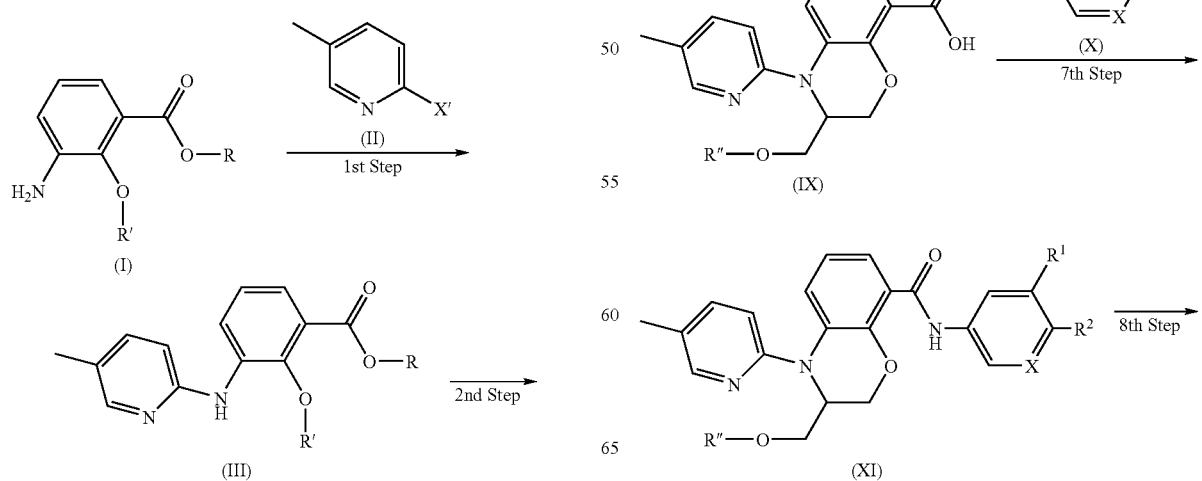

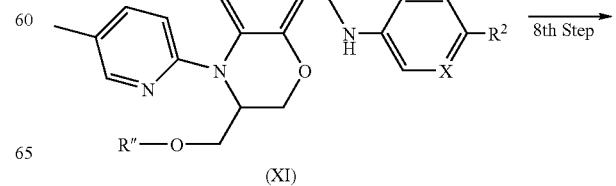

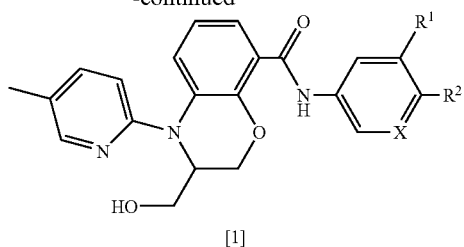

(wherein, R represents a carboxyl protecting group (the carboxyl protecting group here represents a carboxyl protecting group generally used in the art of synthetic organic chemistry and includes, for example, a methyl group, an ethyl group, a propyl group, a tert-butyl group, a benzyl group, a paramethoxy benzyl group, etc.), and forms an ester which is easily led to a carboxylic acid by hydrolysis or catalytic hydrogenation reaction. X' and X" are the same or different and each represents a halogen atom such as chloro and bromo or a sulfonyloxy group such as a 3-nitrobenzene sulfonyloxy group, a p-toluenesulfonyloxy group, a benzene sulfonyloxy group, a p-bromobenzenesulfonyloxy group, a methanesulfonyloxy group or a trifluoromethanesulfonyloxy group. R' represents a protecting group of a phenolic hydroxyl group which can be removed easily by hydrolysis or catalytic hydrogenation reaction (the protecting group of a phenolic hydroxyl group here represents a protecting group of a phenolic hydroxyl group generally used in the art of synthetic organic chemistry and includes, for example, a methoxymethyl group, a methoxyethoxymethyl group, a benzyl group, a tert-butyl group, a tetrahydropyranyl group, an acetyl group, etc.). R" represents a protecting group of a hydroxyl group which can be removed easily by hydrolysis or catalytic hydrogenation reaction (the protecting group of a hydroxyl group here represents a protecting group of a hydroxyl group generally used in the art of synthetic organic chemistry and includes, for example, a methoxymethyl group, a methoxyethoxymethyl group, a benzyl group, a tetrahydropyranyl group, an acetyl group, etc.). Each other symbol is the same as above.)

First Step

This is the step for obtaining a compound (III) by the palladium catalyzed Buchwald/Hartwig type amination reaction from a compound (I) and a compound (II).

The compound (III) can be obtained by reacting the (I) with the compound (II) in toluene, 1,4-dioxane, tetrahydrofuran or the like or a mixed solvent of these, using a palladium catalyst such as a mixture of palladium acetate and 2,2'-bis(diphenylphosphino)-1,1'-binaphthyl, bis(diphenylphosphino)ferrocene palladium chloride (II) or tris(dibenzylideneacetone)dipalladium together with a base such as sodium carbonate, tripotassium phosphate ($K_3PO_4$), potassium carbonate, cesium carbonate, sodium bicarbonate, potassium bicarbonate or potassium tert butoxide, at a temperature of 20° C. to reflux temperature, preferably 60° C. to reflux temperature for 5 hours to 96 hours preferably for 8 hours to 48 hours.

Second Step

This is a step to remove R' from the compound (III) and obtain a compound (IV).

For example, when R' is a methoxymethyl group, benzyloxymethyl group, methoxyethoxymethyl group, tert-butyl group, tetrahydropyranyl group or acetyl group, the compound (IV) can be obtained by reacting the compound (III) without a solvent or in water, methanol, ethanol, propanol, tetrahydrofuran, etc. or a mixed solvent of these using an acid such as hydrochloric acid or trifluoroacetic acid at a temperature of 0° C. to reflux temperature, preferably 0° C. to 50° C. for 0.5 hour to 24 hours, preferably 0.5 hour to 8 hours.

When R' is a benzyl group etc., the compound (IV) can be obtained by the reaction in methanol, ethanol, propanol, tetrahydrofuran or a mixed solvent of these in the presence of palladium carbon catalyst, etc. using hydrogen or ammonium formate at a temperature of about 0° C. to reflux temperature, preferably about 20° C. to reflux temperature for 0.5 hour to 96 hours, preferably 1 hour to 48 hours.

Third Step

This is a step to obtain a compound (VI) by a reaction of the compound (IV) and a compound (V) under basic conditions.

The compound (VI) can be obtained by reacting the compound (IV) and the compound (V), i.e., glycidyl chloride, glycidyl tosylate, glycidyl nosylate, etc. in chloroform, tetrahydrofuran, N,N-dimethylformamide, dimethylsulfoxide, N,N-dimethylacetamide, ethyl acetate, methanol, water or a mixed solvent of these in the presence of a base such as sodium carbonate, potassium carbonate, sodium hydroxide, potassium hydroxide or triethylamine at a temperature of 0° C. to reflux temperature, preferably 0° C. to 60° C. for 0.5 hour to 24 hours.

Fourth Step

This is a step to lead the compound (VI) to a compound (VII) under basic conditions.

The compound (VII) can be obtained by reacting the compound (VI) in chloroform, tetrahydrofuran, N,N-dimethylformamide, N—N-dimethylacetamide, dimethylsulfoxide, ethyl acetate or a mixed solvent of these in the presence of a base such as sodium carbonate, potassium carbonate, sodium hydroxide, potassium hydroxide or triethylamine at a temperature of 0° C. to reflux temperature, preferably 0° C. to 60° C. for 0.5 hour to 24 hours.

Fifth Step

This is a step to remove R from the compound (VII) and obtain a compound (VIII).

For example, when R is a methyl group, ethyl group, propyl group, etc., the compound (VIII) can be obtained by hydrolyzing the compound (VII) in water, methanol, ethanol, propanol, tetrahydrofuran, etc. or a mixed solvent of these using a base such as sodium hydroxide, potassium hydroxide, lithium hydroxide, potassium carbonate or sodium carbonate at a temperature of −20° C. to reflux temperature, preferably 20° C. to reflux temperature for 0.5 hour to 24 hours, preferably 0.5 hour to 8 hours.

For example, when R is a tert-butyl group, the compound (VIII) can be obtained by reacting the compound (VII) without a solvent or in water, methanol, ethanol, propanol, tetrahydrofuran, etc. or a mixed solvent of these using an acid such as hydrochloric acid or trifluoroacetic acid at a temperature of 0° C. to reflux temperature, preferably 0° C. to 50° C. for 0.5 hour to 24 hours, preferably 0.5 hour to 8 hours.

When R is a benzyl group, paramethoxybenzyl group, etc., the compound (VIII) can be obtained by reacting the compound (VII) in methanol, ethanol, propanol, tetrahydrofuran, etc. or a mixed solvent of these using hydrogen or ammonium formate in the presence of a palladium carbon catalyst, etc. at a temperature of about 0° C. to reflux temperature, preferably about 20° C. to 50° C. for 0.5 hour to 96 hours, preferably 1 hour to 48 hours.

Sixth Step

This is a step to protect the hydroxyl group of the compound (VIII) and obtain a compound (IX).

For example, when R" is an acetyl group, the compound (IX) can be obtained by reacting the compound (VIII) in chloroform, tetrahydrofuran, toluene, ethyl acetate, pyridine or without a solvent using acetyl chloride or acetic anhydride in the presence or absence of a base such as pyridine or triethylamine at a temperature of 0° C. to reflux temperature, preferably 0° C. to 50° C. for 0.5 hour to 24 hours, preferably 0.5 hour to 8 hours.

When R" is a tetrahydropyranyl group, the compound (IX) can be obtained by reacting the compound (VIII) in chloroform, tetrahydrofuran, toluene, ethyl acetate or without a solvent using 2,3-dihydropyran in the presence of an acid catalyst such as p-toluenesulfonic acid or hydrogen chloride at a temperature of 0° C. to reflux temperature, preferably 0° C. to 50° C. for 0.5 hour to 24 hours, preferably 0.5 hour to 8 hours.

When R" is a methoxymethyl group, methoxyethoxymethyl group or benzyl group, the compound (IX) can be obtained by reacting the compound (VIII) in a solvent such as tetrahydrofuran or N,N-dimethylformamide using methoxymethyl chloride, methoxyethoxymethyl chloride, benzyl chloride or benzyl bromide in the presence of a base such as sodium hydride or lithium diisopropylamide at a temperature of 0° C. to reflux temperature, preferably 0° C. to 50° C. for 0.5 hour to 24 hours, preferably 0.5 hour to 8 hours.

Seventh Step

This is a step to obtain a compound (XI) by condensation reaction of a compound (IX) and a compound (X).

For example, when a condensation reaction is performed using a condensing agent, a compound (IX) is reacted with a compound (X) in N,N-dimethylformamide, methylene chloride, chloroform etc. or a mixed solvent of these using a condensing agent such as dicyclohexylcarbodiimide or 1-ethyl-3-(3-dimethylaminopropyl)carbodiimide at a temperature of 20° C. to reflux temperature, preferably about 0° C. to 50° C. for 1 hour to 48 hours, preferably about 1 hour to 24 hours to obtain the compound (XI). In this case, additives such as hydroxybenzotriazole or N-hydroxysuccinic acid imide may be added.

When the condensation reaction goes via an acid chloride, the compound (IX) is reacted with thionylchloride, oxalyl chloride, etc. in chloroform, methylene chloride, tetrahydrofuran, etc. or a mixed solvent of these to obtain an acid chloride of (IX) and this is reacted with a compound (X) in toluene, chloroform, tetrahydrofuran or a mixed solvent of these in the presence of a base such as triethylamine or pyridine at a temperature of −20° C. to reflux temperature, preferably about 0° C. to 40° C. for 0.5 hour to 24 hours, preferably about 0.5 hour to 12 hours to obtain the compound (XI).

Eighth Step

This is a step to deprotect the protecting group of the hydroxyl group of the compound (XI) and obtain a compound represented by the general formula [1].

For example, when R" is an acetyl group, the compound represented by the general formula [1] can be obtained by reacting the compound (XI) in tetrahydrofuran, ethanol, methanol, isopropanol, water or a mixed solvent of these in the presence of a base such as lithium hydroxide, sodium hydroxide, potassium hydroxide or potassium carbonate at a temperature of −20° C. to reflux temperature, preferably about 0° C. to 40° C. for 0.5 hour to 24 hours, preferably 0.5 hour to 12 hours.

When R" is a methoxymethyl group, methoxyethoxymethyl group, tetrahydropyranyl group or acetyl group, the compound represented by the general formula [1] can be obtained by reacting the compound (XI) without a solvent or in water methanol, ethanol, propanol, tetrahydrofuran, etc. or a mixed solvent of these using an acid such as hydrochloric acid or trifluoroacetic acid at a temperature of 0° C. to reflux temperature, preferably 0° C. to 50° C. for 0.5 hour to 24 hours, preferably 0.5 hour to 8 hours.

When R" is a benzyl group, the compound represented by the general formula [1] can be obtained by reacting the compound (XI) in methanol, ethanol, propanol, tetrahydrofuran, etc. or a mixed solvent of these using hydrogen or ammonium formate in the presence of a palladium carbon catalyst, etc. at a temperature of about 0° C. to reflux temperature, preferably about 20° C. to 50° C. for 0.5 hour to 96 hours, preferably 1 hour to 48 hours.

Therefore, the compounds represented by the above-mentioned general formulas (I) to (XI) are useful as intermediates for producing the compound of the present invention represented by the general formula [1]

2. Preparation Method B;

This is a method of preparing the compound of the present invention represented by the general formula [1] which is led directly from the compound (VIII) without protecting the hydroxyl group.

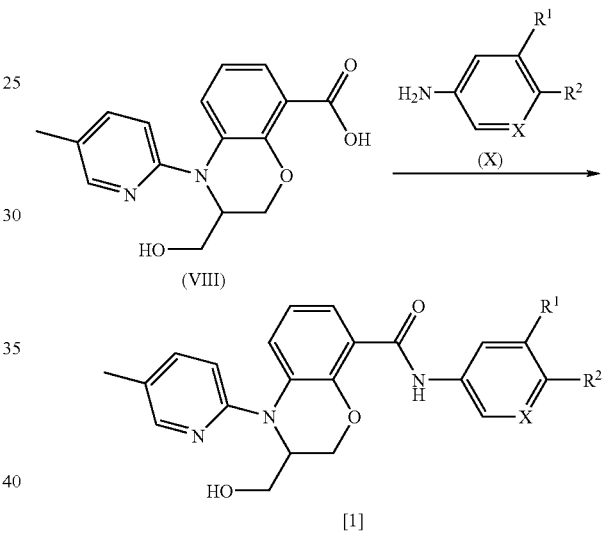

(wherein each symbol is the same as above.)

The compound of the present invention represented by the general formula [1] can be obtained by reacting the compound (VIII) with a compound (X) in N,N-dimethylformamide, methylene chloride, chloroform, etc. or a mixed solvent of these using a condensing agent such as dicyclohexylcarbodiimide or 1-ethyl-3-(3-dimethylaminopropyl)-carbodiimide at a temperature of −20° C. to reflux temperature, preferably about 0° C. to 50° C. for 1 hour to 48 hours, preferably about 1 hour to 24 hours. In this case, an additive such as hydroxybenzotriazole or N-hydroxysuccinic acid imide may be added.

3. Preparation Method C

The salt of the compound of the present invention represented by the general formula [1] can be prepared according to a usual method, for example, as follows:

The compound of the present invention represented by the general formula [1] is dissolved or suspended in a solvent (e.g. water, methanol, ethanol, isopropyl alcohol, acetone, 2-butanone, tetrahydrofuran, ethyl acetate, isobutyl acetate, diethyl ether, diisopropyl ether, toluene, n-hexane, n-heptane or a mixed solvent of these) and supplemented with a solid, undiluted or diluted solution form (as a dilution solvent, e.g. water, methanol, ethanol, isopropyl alcohol, acetone, 2-butanone, tetrahydrofuran, ethyl acetate, isobutyl acetate, diethyl ether, diisopropyl ether, toluene, n-hexane, n-heptane or a mixed solvent of these) of hydroacid (e.g. hydrochloric acid, hydrobromic acid, sulfuric acid, methanesulfonic acid, ethanesulfonic acid, p-toluenesulfonic acid, benzenesulfonic acid, naphthalene-1,5-disulfonic acid, naphthalene-2-sulfonic acid, fumaric acid or maleic acid, etc.), and the mixture can be stirred or left standing at −20° C. to reflux temperature, preferably about 0° C. to 50° C. for 1 hour to 48 hours, preferably about 1 hour to 24 hours to obtain the salt of the compound of the present invention represented by the general formula [1].

EXAMPLES

Next, the production of a compound of the present invention will be described specifically with reference to Examples. However, the present invention is not intended to be limited to these Examples. The NMR data of each compound produced is described along therewith.

Example 1-1

Production of (S)-4-(5-picoline-2-yl)-3-hydroxymethyl-N-(4-tert-butoxy-3,5-difluorophenyl)-3,4-dihydro-2H-benzo[1,4]oxazine-8-carboxamide First Step Production of methyl 3-nitrosalicylate 3-Nitrosalicylic acid (500 g) was dissolved in methanol (2.25 L), concentrated sulfuric acid (0.25 L) was added, and the mixture was refluxed for 22 hours. The reaction solution was cooled on ice, and the precipitated solid was collected by filtration and dried to obtain the title compound (517.3 g).
(400 MHz, DMSO-d6): 3.95 (s, 3H), 7.16 (t, J=8.1 Hz, 1H), 8.11 (dd, J=7.9, 1.9 Hz, 1H), 8.21 (dd, J=8.3, 1.9 Hz, 1H), 11.49 (s, 1H).

Second Step

Production of methyl 2-(2-methoxyethoxy)methyloxy-3-nitrobenzoate

Methyl 3-nitrosalicylate (516.3 g) obtained in the preceding step was dissolved in N,N-dimethylformamide (2.0 L), potassium carbonate (362 g) was added, 1-chloromethoxy-2-methoxyethane (0.329 L) was further added with stirring under ice-cooling, and the mixture was stirred at room temperature for 1 hour. The reaction solution was partitioned between water and ethyl acetate, and the ethyl acetate layer was washed with water and then concentrated to obtain the title compound (706.9 g).
(400 MHz, DMSO-d6): 3.22 (s, 3H), 3.41-3.43 (m, 2H), 3.65-3.68 (m, 2H), 3.87 (s, 3H), 5.16 (s, 2H), 7.47 (t, J=7.9 Hz, 1H), 8.06 (dd, J=7.9, 1.8 Hz, 1H), 8.11 (dd, J=7.9, 1.8 Hz, 1H).

Third Step

Production of methyl 3-amino-2-(2-methoxyethoxy)methyloxybenzoate

Methyl 2-(2-methoxyethoxy)methyloxy-3-nitrobenzoate (704.5 g) obtained in the preceding step was dissolved in ethyl acetate (1 L) and tetrahydrofuran (1 L), 5% palladium carbon (water content 50%) (35 g) was added, and the mixture was stirred for 4 hours under hydrogen atmosphere. The obtained reaction solution was filtered, and the filtrate was concentrated to obtain the title compound (617.7 g).
(400 MHz, DMSO-d6): 3.24 (s, 3H), 3.46-3.48 (m, 2H), 3.78-3.79 (m, 5H), 4.98 (s, 2H), 5.16 (s, 2H), 6.84-6.84 (m, 1H), 6.88-6.91 (m, 2H).

Fourth Step

Production of methyl 3-(5-picoline-2-yl)aminosalicylate;

Cesium carbonate (415 g), palladium acetate (8.8 g), 2,2'-bis(diphenylphosphino)-1,1'-binaphthyl (25 g), methyl 3-amino-2-(2-methoxyethoxy)methyloxybenzoate (200 g) obtained in the preceding step, and 2-chloro-5-picoline (103 g) were added to toluene (1 L) in this order and stirred at 100° C. for 2 days. The reaction solution was filtered, and the filtrate was concentrated. Methanol (500 mL) and 6 N hydrochloric acid (200 mL) were added to the residue, and the mixture was refluxed and stirred for 0.5 hour. Active charcoal (25 g) was added to the reaction solution, and the mixture was stirred for 1 hour and then filtered. 1 N potassium citrate (2 L) was added to the filtrate, and the precipitated crystal was collected by filtration (218 g). The crystal collected by filtration was dissolved in ethyl acetate (1 L) and supplemented with silica gel (100 g), and the mixture was stirred at room temperature and then filtered. The filtrate was concentrated. The residue was recrystallized with acetone:water (2:1) (2 L), and the crystal was filtered and dried to obtain the title compound (128 g).
(400 MHz, DMSO-d6): 2.18 (s, 3H), 3.92 (s, 3H), 6.89 (t, J=8.0 Hz, 1H), 7.04 (d, J=8.6 Hz, 1H), 7.35 (dd, J=7.9, 1.5 Hz, 1H), 7.42 (dd, J=8.4, 2.4 Hz, 1H), 7.98 (s, 1H), 8.19 (s, 1H), 8.48 (dd, J=8.2, 1.5 Hz, 1H), 11.30 (s, 1H).

Fifth Step

Production of methyl(R)-2-(oxirane-2-yl)methyloxy-3-(5-picoline-2-yl)aminobenzoate;

Methyl 3-(5-picoline-2-yl)aminosalicylate (139.5 g) obtained in the preceding step and (R)-glycidyl nosylate (139.7 g) were dissolved in dimethylsulfoxide (700 mL) potassium carbonate (74.6 g) was added, and the mixture was stirred at room temperature for 1 hour. Ethyl acetate (1 L) was added to the reaction solution, and the mixture was filtered. The filtrate was washed with water, then dried over anhydrous sodium sulfate and then concentrated. The residue was suspended in 2-propanol (400 mL), and the suspension was stirred at room temperature and crystallized. The crystal was collected by filtration and dried to obtain the title compound (124 g).
(400 MHz, DMSO-d6): 2.19 (s, 3H), 2.76 (q, J=2.6 Hz, 1H), 2.86 (dd, J=5.0, 4.3 Hz, 1H), 3.40-3.41 (m, 1H), 3.86 (s, 3H), 3.93 (q, J=5.7 Hz, 1H), 4.16 (dd, J=11.2, 2.6 Hz, 1H), 6.94 (d, J=8.4 Hz, 1H), 7.16 (t, J=7.9 Hz, 1H), 7.24 (dd, J=7.7, 1.8 Hz, 1H), 7.46 (dd, J=8.5, 2.3 Hz, 1H), 8.01 (d, J=2.2 Hz, 1H), 8.19 (s, 1H), 8.53 (dd, J=8.2, 1.8 Hz, 1H).

Sixth Step

Production of (S)-methyl 4-(5-picoline-2-yl)-3-hydroxymethyl-3,4-dihydro-2H-benzo[1,4]oxazine-8-carboxylate Methyl(R)-2-(oxirane-2-yl)methyloxy-3-(5-picoline-2-yl)aminobenzoate (124 g) obtained in the preceding step was dissolved in N,N-dimethylacetamide (1.24 L), potassium carbonate (81.8 g) was added, and the mixture was stirred at 100° C. for 2 hours. The reaction solution was partitioned between water and ethyl acetate, and the ethyl acetate layer was washed with water, then dried over anhydrous magnesium sulfate and concentrated to obtain the title compound (142.1 g).

(400 MHz, DMSO-d6): 2.23 (s, 3H), 3.57-3.62 (m, 1H), 3.80 (s, 3H), 3.98-4.00 (m, 1H), 4.06-4.11 (m, 1H), 4.36-4.38 (m, 1H), 4.55 (d, J=10.8 Hz, 1H), 5.15 (t, J=5.4 Hz, 1H), 6.84 (t, J=7.9 Hz, 1H), 7.17-7.18 (m, 2H), 7.35 (d, J=8.2 Hz, 1H), 7.53 (d, J=8.4 Hz, 1H), 8.15 (s, 1H).

Seventh Step

Production of (S)-4-(5-picoline-2-yl)-3-hydroxymethyl-3,4-dihydro-2H-benzo[1,4]oxazine-8-carboxylic acid (S)-methyl 4-(5-picoline-2-yl)-3-hydroxymethyl-3,4-dihydro-2H-benzo[1,4]oxazine-8-carboxylate (142 g) obtained in the preceding step was dissolved in methanol (700 mL), 4 N sodium hydroxide (150 mL) was added, and the mixture was refluxed and stirred for 2 hours. The reaction solution was concentrated, neutralized with 6 N hydrochloric acid and then extracted with ethyl acetate. The ethyl acetate layer was washed with water, dried over anhydrous magnesium sulfate and then concentrated. Ethyl acetate (50 mL) and diisopropyl ether (400 mL) were added to the residue, and the precipitated solid was filtered and dried to obtain the title compound (101.6 g).

(400 MHz, DMSO-d6): 2.23 (s, 3H), 3.38 (t, J=9.9 Hz, 1H), 3.59 (dd, J=10.6, 5.7 Hz, 1H), 3.98 (dd, J=10.8, 2.6 Hz, 1H), 4.37-4.39 (m, 1H), 4.55 (dd, J=10.9, 1.2 Hz, 1H), 5.14 (br s, 1H), 6.82 (t, J=7.9 Hz, 1H), 7.16-7.18 (m, 2H), 7.32 (dd, J=8.2, 1.5 Hz, 1H), 7.53 (dd, J=8.4, 2.4 Hz, 1H), 8.14-8.14 (m, 1H), 12.66 (br s, 1H).

Eighth Step

Production of (S)-4-(5-picoline-2-yl)-3-hydroxymethyl-N-(4-tert-butoxy-3,5-difluorophenyl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (400 mg) obtained in the preceding step was dissolved in N,N-dimethylformamide (2 mL). 4-Tert-butoxy-3,5-difluoroaniline (268 mg), 1-hydroxybenzotriazole (204 mg) and 1-ethyl-3-(3-dimethylaminopropyl)-carbodiimide hydrochloride (281 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=4:3) to obtain the title compound (364 mg).

Example 1-2

Production of (S)-4-(5-picoline-2-yl)-3-hydroxymethyl-N-(3,5-difluoro-4-isopropoxyphenyl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (400 mg) obtained in the Seventh Step of Example 1-1 was dissolved in N,N-dimethylformamide (2 mL). 3,5-Difluoro-4-isopropoxyaniline (249 mg), 1-hydroxybenzotriazole (204 mg) and 1-ethyl-3-(3-dimethylaminopropyl)-carbodiimide hydrochloride (281 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=4:3) to obtain the title compound (332 mg).

Example 1-3

Production of (S)-4-(5-picoline-2-yl)-3-hydroxymethyl-N-(3,5-difluoro-4-ethoxyphenyl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (400 mg) obtained in the Seventh Step of Example 1-1 was dissolved in N,N-dimethylformamide (2 mL). 3,5-Difluoro-4-ethoxyaniline (230 mg), 1-hydroxybenzotriazole (204 mg) and 1-ethyl-3-(3-dimethylaminopropyl)-carbodiimide hydrochloride (281 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=5:4) to obtain the title compound (358 mg).

Example 1-4

Production of (S)-4-(5-picoline-2-yl)-3-hydroxymethyl-N-[2-(2,2-dimethylpropyloxy)pyridine-5-yl]-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (300 mg) obtained in the Seventh Step of Example 1-1 was dissolved in N,N-dimethylformamide (3 mL). 5-Amino-2-(2,2-dimethylpropyloxy)pyridine hydrochloride (253 mg), triethylamine (0.14 mL) and 1-ethyl-3-(3-dimethylaminopropyl)-carbodiimide hydrochloride (211 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography to obtain the title compound (340 mg).

Example 1-5

Production of (S)-4-(5-picoline-2-yl)-3-hydroxymethyl-N-(2-tert-butoxypyridine-5-yl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (148 mg) obtained in the Seventh Step of Example 1-1 was dissolved in N,N-dimethylformamide (5 mL). 5-Amino-2-tert-butoxypyridine (82 mg) and 1-ethyl-3-(3-dimethylaminopropyl)-carbodiimide hydrochloride (103 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The obtained residue was purified by silica gel chromatography (hexane:ethyl acetate=1:1) to obtain the title compound (94 mg).

Example 1-6

Production of (S)-4-(5-picoline-2-yl)-3-hydroxymethyl-N-[2-(2,2,2-trifluoroethyloxy)pyridine-5-yl]-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (150 mg) obtained in the Seventh Step of Example 1-1 was dissolved in N,N-dimethylformamide (1.5 mL). 5-Amino-2-(2,2,2-trifluoroethyloxy)pyridine hydrochloride (114 mg), triethylamine (0.07 mL) and 1-ethyl-3-(3-dimethylaminopropyl)-carbodiimide hydrochloride (105 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The obtained residue was purified by silica gel chromatography (hexane:ethyl acetate=1:1) to obtain the title compound (154 mg).

Example 1-7

Production of (S)-4-(5-picoline-2-yl)-3-hydroxymethyl-N-(2-isobutoxypyridine-5-yl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (388 mg) obtained in the Seventh Step of Example 1-1 was dissolved in N,N-dimethylformamide (4 mL). 5-Amino-2-isobutoxypyridine hydrochloride (262 mg), triethylamine (0.18 mL) and 1-ethyl-3-(3-dimethylaminopropyl)-carbodiimide hydrochloride (272 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=1:1) to obtain the title compound (402 mg).

Example 1-8

Production of (S)-4-(5-picoline-2-yl)-3-hydroxymethyl-N-[3,5-difluoro-4-(2,2,2-trifluoroethoxy)phenyl]-3,4-dihydro-2H-benzo[1,4]oxazine-8-carboxamide First Step Production of (S)-3-acetoxymethyl-4-(5-picoline-2-yl)-3,4-dihydro-2H-benzo[1,4]oxazine-8-carboxylic acid;

(S)-4-(5-picoline-2-yl)-3-hydroxymethyl-3,4-dihydro-2H-benzo[1,4]oxazine-8-carboxylic acid (24.1 g) obtained in the Seventh Step of Example 1-1 was dissolved in tetrahydrofuran (240 mL). 4-(Dimethylamino)pyridine (9.8 g) and acetic anhydride (7.6 mL) were added and the mixture was stirred at room temperature for 0.5 hour. The reaction solution was partitioned between ethyl acetate and a diluted citric acid solution, and the ethyl acetate layer was washed with water, then dried over anhydrous magnesium sulfate and concentrated. Diisopropyl ether was added to the concentrated residue, and the precipitated crystal was collected by filtration and dried to obtain the title compound (23.33 g).

(400 MHz, DMSO-d6) 1.99 (s, 3H), 2.23 (s, 3H), 4.03-4.11 (m, 2H), 4.18-4.21 (m, 1H), 4.48 (d, J=11.25 Hz, 1H), 4.72-4.74 (m, 1H), 6.86 (dd, J=7.61, 7.61 Hz, 1H), 7.17-7.20 (m, 2H), 7.33 (dd, J=8.16, 0.88 Hz, 1H), 7.54 (dd, J=8.49, 2.32 Hz, 1H), 8.15 (d, J=1.54 Hz, 1H), 12.64 (br s, 1H).

Second Step

Production of (S)-3-acetoxymethyl-4-(5-picoline-2-yl)-N-[3,5-difluoro-4-(2,2,2-trifluoroethoxy)phenyl]-3,4-dihydro-2H-benzo[1,4]oxazine-8-carboxamide (S)-3-acetoxymethyl-4-(5-picoline-2-yl)-3,4-dihydro-2H-benzo[1,4]oxazine-8-carboxylic acid (400 mg) obtained in the preceding step was dissolved in tetrahydrofuran (4 mL), thionyl chloride (0.102 mL) was added with stirring under ice-cooling, and the mixture was stirred for 1.5 hours. The reaction solution was concentrated, and the residue was diluted with tetrahydrofuran (4 mL). Triethylamine (0.245 mL) and 3,5-difluoro-4-(2,2,2-trifluoroethoxy)aniline (267 mg) were added with stirring at room temperature and the mixture was stirred for 0.5 hour. The reaction solution was partitioned between water and ethyl acetate, and the ethyl acetate layer was washed with a saturated sodium chloride solution, then dried over anhydrous magnesium sulfate and concentrated to obtain the title compound (749 mg).

(400 MHz, DMSO-d6) 1.99 (s, 3H), 2.25 (s, 3H), 4.12-4.16 (m, 2H), 4.22-4.25 (m, 1H), 4.52 (d, J=11.25 Hz, 1H), 4.75-4.77 (m, 3H), 6.93 (dd, J=7.94, 7.94 Hz, 1H), 7.12 (d, J=7.72 Hz, 1H), 7.19 (d, J=8.60 Hz, 1H), 7.36 (d, J=8.16 Hz, 1H), 7.56-7.58 (m, 3H), 8.17 (d, J=1.54 Hz, 1H), 10.47 (s, 1H).

Third Step

Production of (S)-4-(5-picoline-2-yl)-3-hydroxymethyl-N-[3,5-difluoro-4-(2,2,2-trifluoroethoxy)phenyl]-3,4-dihydro-2H-benzo[1,4]oxazine-8-carboxamide (S)-3-acetoxymethyl-4-(5-picoline-2-yl)-N-[3,5-difluoro-4-(2,2,2-trifluoroethoxy)phenyl]-3,4-dihydro-2H-benzo-[1,4]oxazine-8-carboxamide (749 mg) obtained in the preceding step was dissolved in methanol (4 mL), 4 N sodium hydroxide (0.35 mL) was added, and the mixture was stirred at room temperature for 0.5 hour. The reaction solution was concentrated and then partitioned between water and ethyl acetate, and the obtained ethyl acetate layer was washed with a saturated sodium chloride solution, then dried over anhydrous magnesium sulfate and concentrated. The residue was purified by silica gel chromatography to obtain the title compound (340 mg).

Example 1-9

Production of (S)-4-(5-picoline-2-yl)-3-hydroxymethyl-N-[3,5-difluoro-4-(2-hydroxy-2-methylpropyloxy)phenyl]-3,4-dihydro-2H-benzo[1,4]oxazine-8-carboxamide First Step Production of (S)-4-(5-picoline-2-yl)-3-hydroxymethyl-N-(3,5-difluoro-4-hydroxyphenyl)-3,4-dihydro-2H-benzo[1,4]oxazine-8-carboxamide (S)-4-(5-picoline-2-yl)-3-hydroxymethyl-3,4-dihydro-2H-benzo[1,4]oxazine-8-carboxylic acid (900 mg) obtained in the Seventh Step of Example 1-1 was dissolved in N,N-dimethylformamide (4.5 mL). 3,5-Difluoro-4-hydroxyaniline (330 mg) and 1-ethyl-3-(3-dimethylaminopropyl)-carbodiimide hydrochloride (630 mg) were added in this order and the mixture was stirred overnight at room temperature. Water and a saturated sodium hydrogencarbonate solution were added to the reaction solution and then extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=1:1) to obtain the title compound (550 mg).

(400 MHz, DMSO-d6) 2.25 (s, 3H), 3.44-3.46 (m, 1H), 3.63-3.65 (m, 1H), 4.05-4.08 (m, 1H), 4.39-4.41 (m, 1H), 4.60 (d, J=9.74 Hz, 1H), 5.15 (br s, 1H), 6.89 (dd, J=7.88, 7.88 Hz, 1H), 7.10 (dd, J=7.65, 1.62 Hz, 1H), 7.21 (d, J=8.35 Hz, 1H), 7.34 (dd, J=8.12, 1.62 Hz, 1H), 7.46-7.49 (m, 2H), 7.56 (dd, J=8.35, 1.86 Hz, 1H), 8.17 (dd, J=1.16, 1.16 Hz, 1H), 9.91 (br s, 1H), 10.23 (s, 1H).

Second Step

Production of (S)-4-(5-picoline-2-yl)-3-hydroxymethyl-N-[3,5-difluoro-4-(ethoxycarbonylmethyloxy)phenyl]-3,4-dihydro-2H-benzo[1,4]oxazine-8-carboxamide (S)-4-(5-picoline-2-yl)-3-hydroxymethyl-N-(3,5-difluoro-4-hydroxyphenyl)-3,4-dihydro-2H-benzo[1,4]oxazine-8-carboxamide (459 mg) obtained in the preceding step was dissolved in N,N-dimethylformamide (4.5 mL). Potassium carbonate (150 mg) and ethyl bromoacetate (180 mg) were added and the mixture was stirred at 60° C. for 3 hours. The reaction solution was partitioned between water and ethyl acetate. The ethyl acetate layer was washed with a saturated sodium chloride solution, dried over anhydrous magnesium sulfate and then concentrated. The residue was purified by silica gel chromatography (hexane:ethyl acetate=2:3) to obtain the title compound (310 mg).

(400 MHz, DMSO-d6) 1.21 (t, J=7.06 Hz, 3H), 2.24 (s, 3H), 3.43-3.45 (m, 1H), 3.60-3.65 (m, 1H), 4.04-4.08 (m, 1H), 4.16 (q, J=7.06 Hz, 2H), 4.38-4.39 (m, 1H), 4.59 (d, J=10.81 Hz, 1H), 4.79 (s, 2H), 5.12 (t, J=5.51 Hz, 1H), 6.89 (dd, J=7.83, 7.83 Hz, 1H), 7.08 (dd, J=7.50, 1.32 Hz, 1H), 7.20 (d, J=8.60 Hz, 1H), 7.33 (dd, J=8.16, 1.32 Hz, 1H), 7.52-7.56 (m, 3H), 8.16 (d, J=2.43 Hz, 1H), 10.39 (s, 1H).

Third Step

Production of (S)-4-(5-picoline-2-yl)-3-hydroxymethyl-N-[3,5-difluoro-4-(2-hydroxy-2-methylpropyloxy)phenyl]-3,4-dihydro-2H-benzo[1,4]oxazine-8-carboxamide;

(S)-4-(5-picoline-2-yl)-3-hydroxymethyl-N-[3,5-difluoro-4-(ethoxycarbonylmethyloxy)phenyl]-3,4-dihydro-2H-benzo[1,4]oxazine-8-carboxamide (310 mg) obtained in the preceding step was dissolved in tetrahydrofuran (3.1 mL), and methyllithium (0.98 M tetrahydrofuran solution) (3.7 mL) was added dropwise with stirring under ice-cooling and then stirred for 1.5 hours. The reaction solution was poured to 5% citric acid solution and extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=1:3) to obtain the title compound (72 mg).

Example 1-10

Production of (S)-4-(5-picoline-2-yl)-3-hydroxymethyl-N-[3,5-difluoro-4-(1,1-dimethyl-2-hydroxyethyloxy)phenyl]-3,4-dihydro-2H-benzo[1,4]oxazine-8-carboxamide First Step Production of (S)-4-(5-picoline-2-yl)-3-hydroxymethyl-N-[3,5-difluoro-4-(1-ethoxycarbonyl-1-methyl)ethyloxyphenyl]-3,4-dihydro-2H-benzo[1,4]oxazine-8-carboxamide (S)-4-(5-picoline-2-yl)-3-hydroxymethyl-N-(3,5-difluoro-4-hydroxyphenyl)-3,4-dihydro-2H-benzo[1,4]oxazine-8-carboxamide (780 mg) obtained in the First Step of Example 1-9 was dissolved in dimethylsulfoxide (7.8 mL). Potassium carbonate (240 mg) and ethyl 2-bromo-2-methylpropionate (0.279 mL) were added and the mixture was stirred at 80° C. for 1 hour. The reaction solution was partitioned between water and ethyl acetate. The ethyl acetate layer was washed with a saturated sodium chloride solution, dried over anhydrous magnesium sulfate and then concentrated. The residue was purified by silica gel chromatography (hexane:ethyl acetate=1:1) to obtain the title compound (740 mg).

(400 MHz, DMSO-d6) 1.24 (t, J=7.19 Hz, 4H), 1.49 (s, 6H), 2.25 (s, 3H), 3.44-3.46 (m, 1H), 3.63-3.66 (m, 1H), 4.06-4.09 (m, 1H), 4.17 (q, J=7.11 Hz, 2H), 4.39-4.41 (m, 1H), 4.60 (d, J=10.20 Hz, 1H), 5.15 (t, J=5.57 Hz, 1H), 6.90 (dd, J=7.88, 7.88 Hz, 1H), 7.09 (dd, J=7.42, 1.39 Hz, 1H), 7.22 (d, J=8.81 Hz, 1H), 7.35 (dd, J=8.12, 1.62 Hz, 1H), 7.53-7.57 (m, 3H), 8.17-8.17 (m, 1H), 10.47 (s, 1H).

Second Step

Production of (S)-4-(5-picoline-2-yl)-3-hydroxymethyl-N-[3,5-difluoro-4-(1-carboxy-1-methyl)ethyloxyphenyl]-3,4-dihydro-2H-benzo[1,4]oxazine-8-carboxamide (S)-4-(5-picoline-2-yl)-3-hydroxymethyl-N-[3,5-difluoro-4-(1-ethoxycarbonyl-1-methyl)ethyloxyphenyl]-3,4-dihydro-2H-benzo[1,4]oxazine-8-carboxamide (740 mg) obtained in the preceding step was dissolved in ethanol (7.4 mL), 4 N sodium hydroxide solution (0.38 mL) was added, and the mixture was stirred overnight at room temperature. The reaction solution was poured to 5% citric acid solution and extracted with tetrahydrofuran. The tetrahydrofuran layer was washed with a saturated sodium chloride solution, dried over anhydrous magnesium sulfate and then concentrated to obtain the title compound (586 mg).

(400 MHz, DMSO-d6) 1.45 (s, 6H), 2.25 (s, 3H), 3.45 (dd, J=9.97, 9.97 Hz, 1H), 3.63-3.64 (m, 1H), 4.06-4.08 (m, 2H), 4.38-4.41 (m, 1H), 4.59 (d, J=10.20 Hz, 1H), 6.90 (dd, J=7.88, 7.88 Hz, 1H), 7.09 (dd, J=7.65, 1.62 Hz, 1H), 7.21 (d, J=8.81 Hz, 1H), 7.35 (dd, J=8.12, 1.62 Hz, 1H), 7.53-7.56 (m, 3H), 8.17 (dd, J=1.16, 0.58 Hz, 1H), 10.45 (s, 1H), 12.94 (br s, 1H).

Third Step

Production of (S)-4-(5-picoline-2-yl)-3-hydroxymethyl-N-[3,5-difluoro-4-(1,1-dimethyl-2-hydroxyethyloxy)phenyl]-3,4-dihydro-2H-benzo[1,4]oxazine-8-carboxamide Triethylamine (0.191 mL), ethyl chlorocarbonate (0.131 mL) and then a suspension of (S)-4-(5-picoline-2-yl)-3-hydroxymethyl-N-[3,5-difluoro-4-(1-carboxy-1-methyl)ethyloxyphenyl]-3,4-dihydro-2H-benzo[1,4]oxazine-8-carboxamide (586 mg) obtained in the preceding step in tetrahydrofuran (5.9 mL) were added to tetrahydrofuran (3 mL) with stirring under ice-cooling and the mixture was stirred at room temperature for 1 hour. The reaction solution was cooled on ice and sodium borohydride (43 mg) and methanol (5.9 mL) were added. The reaction solution was poured to 10% ammonium chloride solution and extracted with ethyl acetate. The ethyl acetate layer was washed with a saturated sodium chloride solution, dried over anhydrous magnesium sulfate and then concentrated. The residue was purified by silica gel chromatography (hexane:ethyl acetate=2:1) to obtain the title compound (136 mg).

Chemical structures and NMR data of compounds obtained in Examples 1-1 to 1-10 are shown in Table 1 and Table 2.

TABLE 1

| Example | Chemical Structure | NMR |
|---|---|---|
| 1-1 | 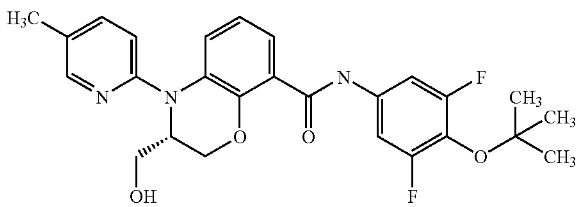 | (400 MHz, DMSO-d6) 1.32 (s, 9H), 2.24 (s, 3H), 3.44-3.47 (m, 1H), 3.62-3.63 (m, 1H), 4.04-4.06 (m, 1H), 4.39 (t, J = 7.28 Hz, 1H), 4.59 (d, J = 10.37 Hz, 1H), 5.11 (l, J = 5.40 Hz, 1H), 6.89 (dd, J = 7.94, 7.94 Hz, 1H), 7.08 (dd, J = 7.39, 1.21 Hz, 1H), 7.20 (d, J = 8.38 Hz, 1H), 7.33 (dd, J = 8.27, 1.43 Hz, 1H), 7.51-7.57 (m, 3H), 8.16 (d, J = 2.43 Hz, 1H), 10.40 (s, 1H). |
| 1-2 | 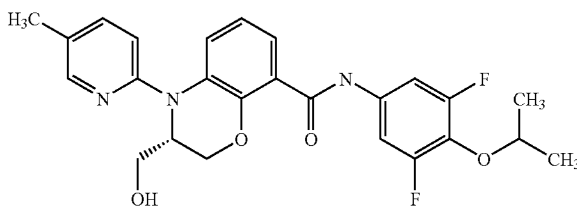 | (400 MHz, DMSO-d6) 1.29 (d, J = 6.03 Hz, 6H), 2.26 (s, 3H), 3.45-3.48 (m, 1H), 3.64-3.66 (m, 1H), 4.08 (dd, J = 10.67, 2.32 Hz, 1H), 4.29-4.35 (m, 1H), 4.39-4.46 (m, 1H), 4.61 (d, J = 10.20 Hz, 1H), 5.15 (t, J = 5.57 Hz, 1H), 6.90 (dd, J = 7.88, 3.94 Hz, 1H), 7.11 (dd, J = 7.65, 1.62 Hz, 1H), 7.22 (d, J = 8.35 Hz, 1H), 7.35 (dd, J = 8.35, 1.39 Hz, 1H), 7.54-7.57 (m, 3H), 8.17 (d, J = 2.32 Hz, 1H), 10.41 (s, 1H). |
| 1-3 | 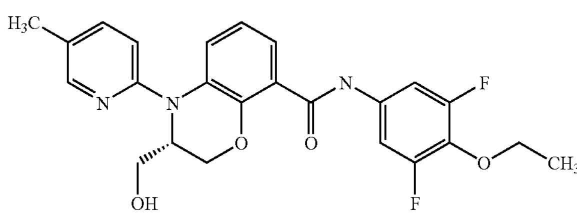 | (400 MHz, DMSO-d6) 1.30 (t, J = 6.96 Hz, 3H), 2.25 (s, 3H), 3.44-3.46 (m, 1H), 3.62-3.64 (m, 1H), 4.11 (q, J = 6.96 Hz, 3H), 4.39-4.41 (m, 1H), 4.59 (d, J = 10.20 Hz, 1H), 5.15 (t, J = 5.57 Hz, 1H), 6.90 (dd, J = 7.88, 7.88 Hz, 1H), 7.09 (dd, J = 7.65, 1.62 Hz, 1H), 7.21 (d, J = 8.81 Hz, 1H), 7.35 (dd, J = 8.35, 1.39 Hz, 1H), 7.53-7.58 (m, 3H), 8.17 (d, J = 2.32 Hz, 1H), 10.41 (s, 1H). |
| 1-4 | 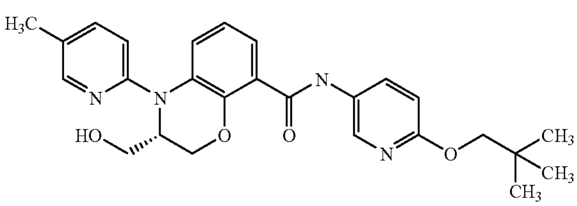 | (400 MHz, DMSO-d6) 0.99 (s, 9H), 2.24 (s, 3H), 3.44 (dt, J = 15.0, 5.3 Hz, 1H), 3.60-3.66 (m, 1H), 3.93 (s, 2H), 4.07 (dd, J = 10.9, 2.6 Hz, 1H), 4.40 (s, 1H), 4.60 (d, J = 9.7 Hz, 1H), 5.14 (t, J = 5.6 Hz, 1H), 6.83-6.90 (m, 2H), 7.13 (dd, J = 7.5, 1.5 Hz, 1H), 7.20 (d, J = 8.6 Hz, 1H), 7.32 (dd, J = 8.2, 1.5 Hz, 1H), 7.55 (dd, J = 9.0, 2.6 Hz, 1H), 8.02 (dd, J = 8.9, 2.7 Hz, 1H), 8.16 (d, J = 2.6 Hz, 1H), 8.48 (d, J = 2.1 Hz, 1H), 10.15 (s, 1H). |
| 1-5 | 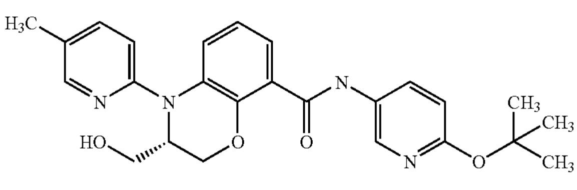 | (400 MHz, DMSO-d6) 1.52 (s, 9H), 2.24 (s, 3H), 3.44 (dt, J = 14.8, 5.2 Hz, 1H), 3.60-3.66 (m, 1H), 4.06 (dd, J = 11.0, 2.7 Hz, 1H), 4.40 (t, J = 7.3 Hz, 1H), 4.60 (d, J = 9.7 Hz, 1H), 5.14 (t, J = 5.6 Hz, 1H), 6.71 (d, J = 8.8 Hz, 1H), 6.88 (t, J = 7.8 Hz, 1H), 7.12 (dd, J = 7.7, 1.6 Hz, 1H), 7.20 (d, J = 8.3 Hz, 1H), 7.32 (d, J = 8.1, 1.6 Hz, 1H), 7.55 (dd, J = 8.8, 2.1 Hz, 1H), 7.99 (dd, J = 8.8, 2.8 Hz, 1H), 8.16 (d, J = 2.3 Hz, 1H), 8.44 (d, J = 2.3 Hz, 1H), 10.13 (s, 1H). |

TABLE 1-continued

| Example | Chemical Structure | NMR |
|---|---|---|
| 1-6 | 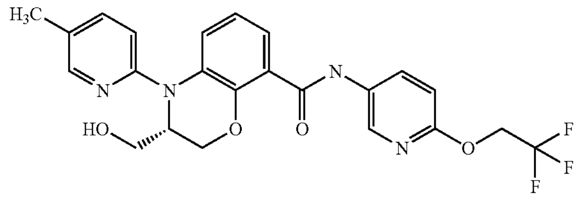 | (400 MHz, DMSO-d6) 2.24 (s, 3H), 3.44 (td, J = 9.9, 6.0 Hz, 1H), 3.60-3.66 (m, 1H), 4.07 (dd, J = 10.9, 2.8 Hz, 1H), 4.40 (l, J = 6.8 Hz, 1H), 4.60 (d, J = 10.0 Hz, 1H), 4.97 (q, J = 9.1 Hz, 2H), 5.14 (t, J = 5.6 Hz, 1H), 6.89 (t, J = 7.9 Hz, 1H), 7.01 (d, J = 8.8 Hz, 1H), 7.13 (dd, J = 7.5, 1.5 Hz, 1H), 7.20 (d, J = 8.6 Hz, 1H), 7.33 (dd, J = 8.2, 1.5 Hz, 1H), 7.55 (dd, J = 8.8, 2.1 Hz, 1H), 8.12 (dd, J = 8.9, 2.7 Hz, 1H), 8.16 (d, J = 2.3 Hz, 1H), 8.56 (d, J = 2.3 Hz, 1H), 10.28 (s, 1H). |
| 1-7 | 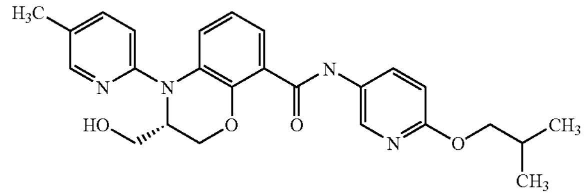 | (400 MHz, DMSO-d6) 0.97 )d, J = 6.7 Hz, 6H), 197-2.07 (m, 1H), 2.24 (s, 3H), 3.45 (dt, J = 15.0, 5.2 Hz, 1H), 3.60-3.66 (m, 1H), 4.01 (d, J = 6.7 Hz, 2H), 4.07 (dd, J = 10.8, 2.4 Hz, 1H), 4.40 (t, J = 7.4 Hz, 1H), 4.60 (dd, J = 10.9, 0.9 Hz, 1H), 5.13 (t, J = 5.6 Hz, 1H), 6.81-6.90 (m, 2H), 7.13 (dd, J = 7.5, 1.5 Hz, 1H), 7.20 (d, J = 8.3 Hz, 1H), 7.32 (dd, J = 8.1, 1.6 Hz, 1H), 7.55 (dd, J = 8.6, 2.1 Hz, 1H), 8.02 (dd, J = 8.9, 2.7 Hz, 1H), 8.16 (d, J = 2.3 Hz, 1H), 8.48 (d, J = 2.3 Hz, 1H), 10.14 (s, 1H). |

TABLE 2

| Example | Chemical Structure | NMR |
|---|---|---|
| 1-8 | 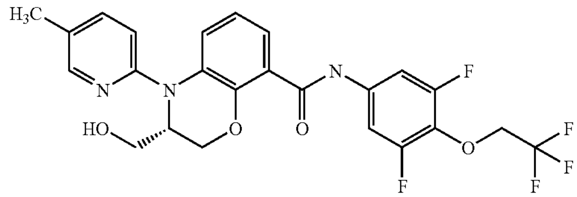 | (400 MHz, DMSO-d6) 2.26 (s, 3H), 3.44-3.46 (m, 1H), 3.61-3.66 (m, 1H), 4.07 (dd, J = 10.90, 2.55 Hz, 1H), 4.39-4.40 (m, 1H), 4.59 (d, J =10.20 Hz, 1H), 4.77 (q, J = 8.97 Hz, 2H), 5.14 (t, J = 5.57 Hz, 1H), 6.90 (dd, J = 7.88, 7.88 Hz, 1H), 7.10 (dd, J = 7.42, 1.39 Hz, 1H), 7.21 (d, J = 8.35 Hz, 1H), 7.35 (dd, J = 8.35, 1.39 Hz, 1H), 7.56-7.61 (m, 3H), 8.17 (d, J = 1.16 Hz, 1H), 10.47 (s, 1H). |
| 1-9 | 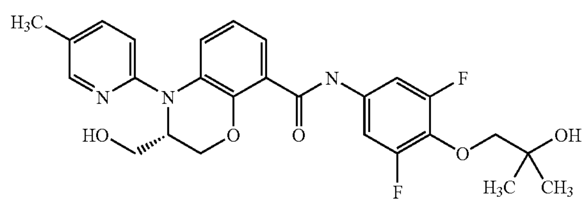 | (400 MHz, DMSO-d6) 1.22 (s, 6H), 2.25 (s, 3H), 3.40-3.48 (m, 1H), 3.61-3.66 (m, 1H), 3.80 (s, 2H), 4.07 (dd, J = 10.90, 2.55 Hz, 1H), 4.39-4.40 (m, 1H), 4.58-4.61 (m, 2H), 5.14 (l, J = 5.57 Hz, 1H), 6.90 (dd, J = 7.88, 7.88 Hz, 1H), 7.09 (dd, J = 7.88, 1.39 Hz, 1H), 7.21 (d, J = 8.81 Hz, 1H), 7.34 (dd, J = 8.12, 1.62 Hz, 1H), 7.52-7.56 (m, 3H), 8.17 (d, J = 2.32 Hz, 1H), 10.39 (s, 1H). |
| 1-10 | 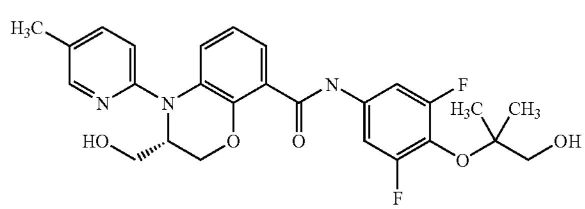 | (400 MHz, DMSO-d6) 1.22 (s, 6H), 2.25 (s, 3H), 3.46-3.48 (m, 3H), 3.61-3.66 (m, 1H), 4.07 (dd, J = 10.90, 2.55 Hz, 1H), 4.39-4.40 (m, 1H), 4.59 (d, J = 10.20 Hz, 1H), 4.93 (t, J = 6.03 Hz, 1H), 5.14 (t, J = 5.57 Hz, 1H), 6.90 (dd, J = 7.88, 3.94 Hz, 1H), 7.08 (dd, J = 7.65, 1.62 Hz, 1H), 7.21 (d, J = 8.81 Hz, 1H), 7.35 (dd, J = 8.12, 1.62 Hz, 1H), 7.53-7.56 (m, 3H), 8.17 (d, J = 2.32 Hz, 1H), 10.43 (s, 1H). |

Test Example

The assay for evaluation of VR1 inhibition by the compounds of the present invention will be described below.

The assay was intended to evaluate in vitro an inhibitory effect on $Ca^{2+}$ entry in cells caused by proton, one of the VR1 agonists (Test Example [1]), a metabolic stability test in liver S9 (Test Example [2]), an in-vitro membrane permeability test (Test Example [3]) and a stability test in Japanese Pharmacopoeia 1 solution (Test Example [4]), using the compound of the present invention and compounds of Comparative Examples shown in Table 3 below. The compounds of Comparative Examples were obtained according to the preparation method described by PCT/JP2005/013446.

TABLE 3

| Comparative Example | Chemical Structure |
|---|---|
| 1 | 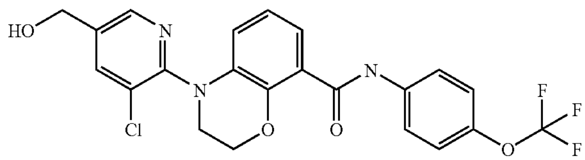 |
| 2 | 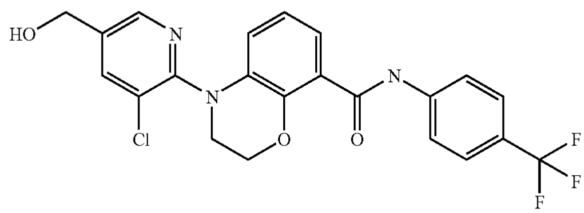 |
| 3 | 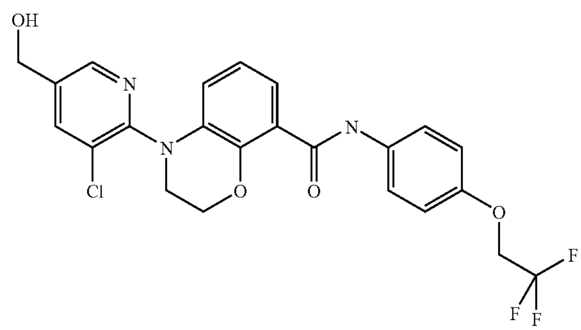 |
| 4 | 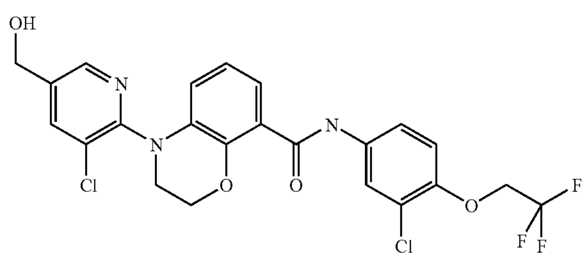 |
| 5 | 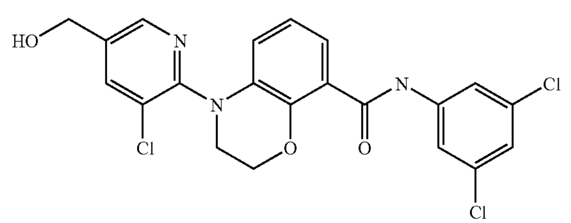 |
| 6 | 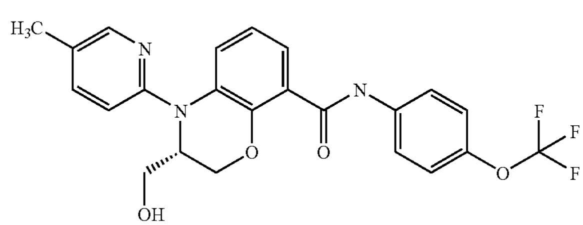 |

TABLE 3-continued

| Comparative Example | Chemical Structure |
|---|---|
| 7 | 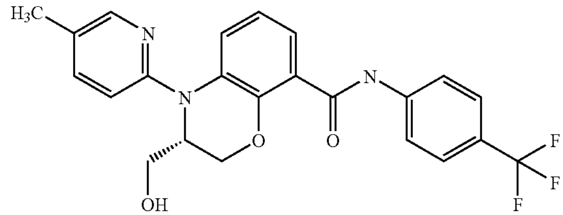 |
| 8 | 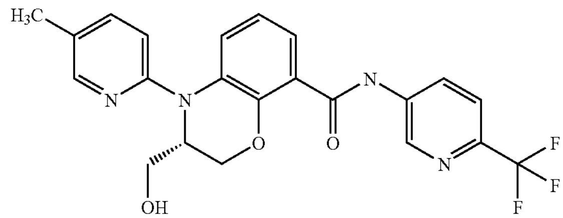 |
| 9 | 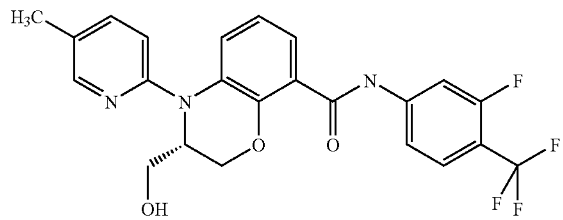 |
| 10 | 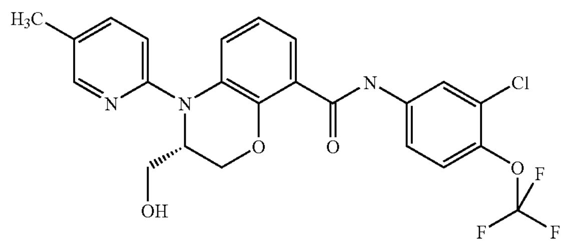 |
| 11 | 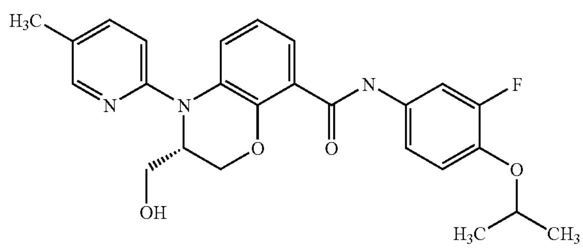 |
| 12 | 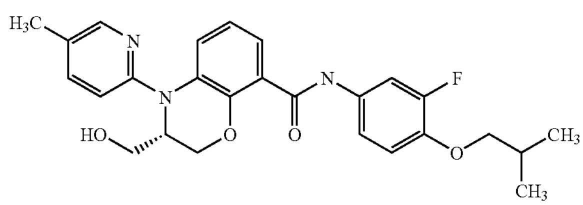 |
| 13 | 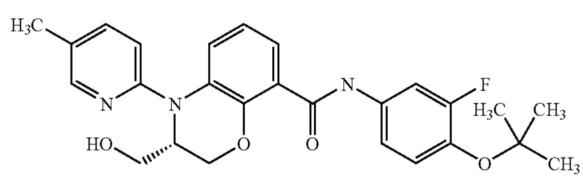 |

Test Example [1]

Inhibition of Ca$^{2+}$ Entry in Cells;

An inhibitory effect on VR1 activity was evaluated by measuring Ca$^{2+}$ uptake in cells.

Rat glioma (C6BU1) cells stably expressing human VR1 were suspended in 20 mM MES buffer (at pH 6.8, contg. 20 mM 2-morpholinoethanesulfonate (referred to as MES hereinafter), 115 mM NaCl, 5 mM KCl, 1 mM MgCl$_2$ and 14 mM D-glucose) to make a cell density of 1×10$^6$ cells/mL. A fluorescent dye, Fura 2-AM solution (Dojindo Corporate, Cat. No. 343-05401) was added to the suspension to make a 5 µM concentration thereof. Further, Pluronic F-127 (Wako Pure Chemical Industries, Ltd., Cat. No. P6866) was added to make a 0.1% content thereof. Then, the suspension was incubated at 37° C. for 30 min. The cells were harvested and washed two times with 20 mM MES buffer. The cells were suspended again to make a cell density of 5×10$^5$ cells/mL. A 500-µL portion of the suspension was taken with a cuvette (MC MEDICAL, INC., Cat. No. SSR3121), to which 10 µL of 20 mM MES buffer containing 250 mM CaCl$_2$ was added to incorporate Ca$^{2+}$ into the cells. At the same time, 5 µL of a test compound solution (in a range of 100 µM to 10 nM in DMSO) was also added to provide a final concentration thereof in a range of 1 µM to 0.1 nM. Alternatively, 5 µL of DMSO was added as control to provide a final concentration of 1% DMSO. The suspension was set in an intracellular ionometer (CAF-110; JASCO) 10 min after those additions. The cells were stimulated with protons by addition of 50 µL of 20 mM MES buffer at pH 1.1 to the suspension to set its pH at 5.7. The activity of the test compound was determined as a difference between the minimum of fluorescence intensity before agonist stimulation and its maximum after the stimulation. The value of IC$_{50}$ was derived from percentage of inhibition by the test compound compared with the control.

Test Example [2]

Metabolic Stability Test in Liver S9;

Human liver S9 (final concentration: 2 mg protein/mL) was suspended in 100 mM potassium phosphate buffer (at pH 7.4, which contained β-nicotinamide adenine dinucleotide phosphate: 1.3 mM, D-glucose-6-phosphate: 3.3 mM, magnesium chloride: 3.3 mM and glucose-6-phosphate dehydrogenase: 0.45 U/mL) and further mixed with the test compound dissolved in DMSO. The mixture was incubated at 37° C. for 0 and 60 minutes and then supplemented with acetonitrile containing formic acid (final concentration 0.1%). The test compound (uncharged) in a supernatant after centrifugation was measured using high-performance liquid chromatography/ mass spectrometry (LC/MS). A remaining ratio (%) was calculated from the obtained measurement value according to the following equation:

Remaining ratio (%)=(amount of test compound after 60 minutes of incubation/amount of test compound on 0 minute of incubation)×100

Test Example [3]

In-Vitro Membrane Permeability Test;

10 mM DMSO solution of the test compound was diluted with Hanks buffer (pH 6.5) to 25 µM to make a test compound solution. 300 µL of Apical buffer (Hanks buffer (pH 6.5)) and 1 mL of Basolateral buffer (4.5% BSA-containing Hanks buffer (pH 7.4)) were added to the apical side (mucosal side) and the basolateral side (serosal side), respectively, of Caco2 cells (cells cultured for 6 days after seeding) seeded onto a plate for permeability test (BIOCOAT HTS Caco2 Assay system: BD Biosciences), and preincubated at 37° C. for 20 minutes, followed by measurement of a transepithelial electrical resistance value. Each buffer on the apical side and basolateral side was removed by aspiration. Then, 300 µL of the test compound solution and 1 mL of Basolateral buffer were added to the apical side and the basolateral side, respectively, and incubated at 37° C. for 2 hours with stirring at 60 rpm. Then, sampling was performed from each of the apical side and the basolateral side, and the sample was supplemented with acetonitrile and centrifuged. The test compound (uncharged) in the supernatant was measured using high-performance liquid chromatography/tandem mass spectrometry (LC/MS/MS: Quantum, Thermo Quest).

A membrane permeability coefficient (Papp) was calculated according to the following equation:

$$Papp(cm/sec.)=(dx/dt)/(A \times C_0)$$

(wherein dx is the amount of the test compound (uncharged) on the basolateral side after incubation, dt is an incubation time, A is the surface area of the cell membrane, and C$_0$ is the initial concentration of the test compound on the apical side.)

Test Example [4]

Stability Test in Japanese Pharmacopoeia 1 Solution;

The test compound was dissolved in a mixed solution of CH$_3$CN and Japanese Pharmacopoeia 1 solution (volume ratio 3:7) and adjusted in a vial for HPLC to a concentration of 0.05 mM. The test compound was measured by HPLC at 40° C. after 0 and 8 hours. The measurement value on 0 hour was defined as 100% to determine the remaining ratio of the test compound after 8 hours.

The "Japanese Pharmacopoeia 1 solution" here represents a solution in which 21 ml of concentrated hydrochloric acid was added to 6 g of sodium chloride and further adjusted to 3 L with distilled water.

The results of the inhibitory effect on Ca$^{2+}$ entry in cells (Test Example [1]), the metabolic stability test in liver S9 (Test Example [2]) and the in-vitro membrane permeability test (Test Example [3]) are shown in Tables 4 to 6 below.

TABLE 4

| Example Comparative Example | Chemical Structure | VRI Inhibition IC50 (nM) | Human liver S9 remaining ratio (%) | membrane permeability Papp (×10⁻⁶ cm/sec) |
| --- | --- | --- | --- | --- |
| Example 1-1 | 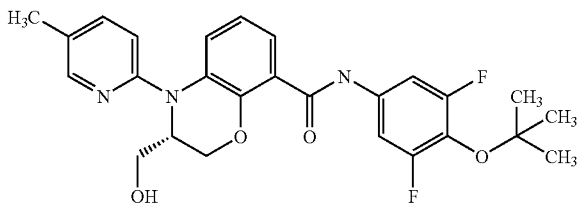 | 0.024 | 90.8 | 8.59 |
| Example 1-2 | 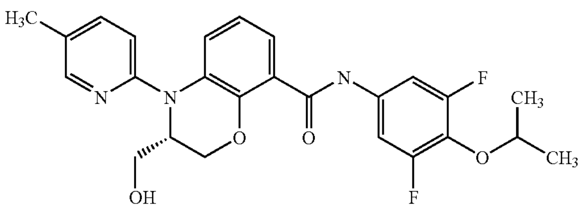 | 0.038 | 65.3 | 20.96 |
| Example 1-3 | 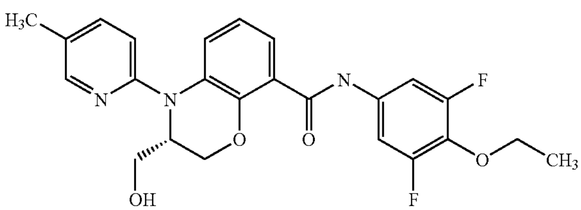 | 0.24 | 59.6 | 26.93 |
| Example 1-4 | 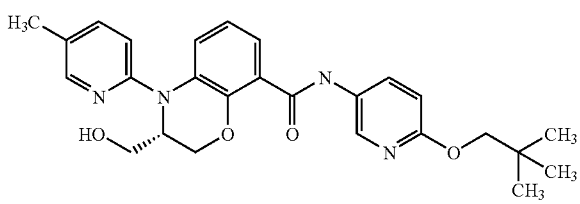 | 0.019 | 39.7 | 30.25 |
| Example 1-5 | 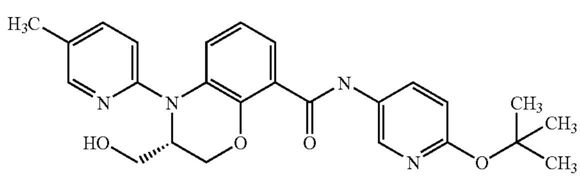 | 0.66 | 82.2 | 38.07 |
| Example 1-6 | 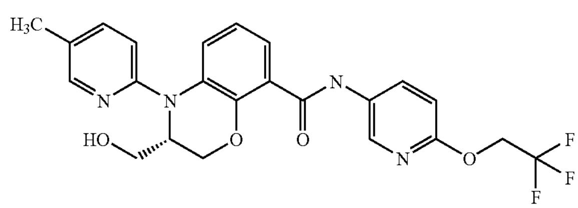 | 0.15 | 91.8 | 37.53 |
| Example 1-7 | 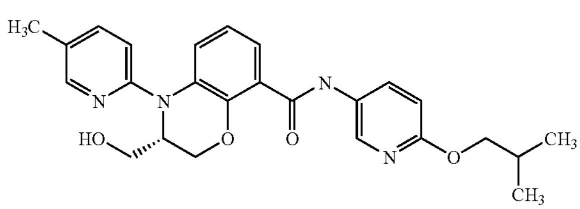 | 0.14 | 50.4 | 37.94 |

TABLE 5

| Example 1-8 | (structure) | 0.038 | 91.5 | 13.61 |
| Example 1-9 | (structure) | 0.54 | 77.3 | 50.36 |
| Example 1-10 | (structure) | 0.69 | 92.2 | 39.22 |
| Comparative Example 1 | (structure) | 3 | 86.3 | 27.1 |
| Comparative Example 2 | (structure) | 1.3 | 90.1 | 24.2 |
| Comparative Example 3 | (structure) | 18 | 89.4 | 25.6 |
| Comparative Example 4 | (structure) | 5.2 | 92.5 | 5.3 |

TABLE 5-continued

| | Structure | | | |
|---|---|---|---|---|
| Comparative Example 5 | [structure: 4-(5-(hydroxymethyl)-3-chloropyridin-2-yl)-N-(3,5-dichlorophenyl)-3,4-dihydro-2H-benzo[b][1,4]oxazine-8-carboxamide] | 42.0 | 64.9 | 7.9 |

TABLE 6

| | Structure | | | |
|---|---|---|---|---|
| Comparative Example 6 | [structure with 5-methylpyridine, hydroxymethyl benzoxazine, N-(4-(trifluoromethoxy)phenyl)carboxamide] | 0.3 | 77.3 | 21.1 |
| Comparative Example 7 | [structure with 5-methylpyridine, hydroxymethyl benzoxazine, N-(4-(trifluoromethyl)phenyl)carboxamide] | 0.4 | 55.1 | 18.2 |
| Comparative Example 8 | [structure with 5-methylpyridine, hydroxymethyl benzoxazine, N-(6-(trifluoromethyl)pyridin-3-yl)carboxamide] | 7 | 62.9 | 43.1 |
| Comparative Example 9 | [structure with 5-methylpyridine, hydroxymethyl benzoxazine, N-(3-fluoro-4-(trifluoromethyl)phenyl)carboxamide] | 0.12 | 65.9 | 19.4 |
| Comparative Example 10 | [structure with 5-methylpyridine, hydroxymethyl benzoxazine, N-(3-chloro-4-(trifluoromethoxy)phenyl)carboxamide] | 0.04 | 82.3 | 6.7 |

TABLE 6-continued

| | | | | |
|---|---|---|---|---|
| Comparative Example 11 | 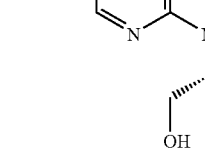 | 0.36 | 66.7 | 40.3 |
| Comparative Example 12 | 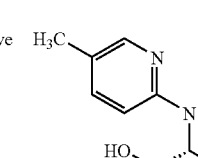 | 0.03 | 54.5 | 10.4 |
| Comparative Example 13 | 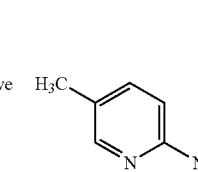 | 0.12 | 91.3 | 28.6 |

[1] Discussion about Test Result of Inhibitory Effect on $Ca^{2+}$ Entry in Cells (Test Example [1]);

The values of $IC_{50}$ of the compounds of Examples 1-1 to 1-10 included in the compound of the present invention represented by the general formula [1] were, as shown in Tables 4 to 6, 0.024 nM, 0.038 nM, 0.24 nM, 0.019 nM, 0.66 nM, 0.15 nM, 0.14 nM, 0.038 nM, 0.54 nM and 0.69 nM, respectively, and the average value of $IC_{50}$ of these ten compounds was 0.25 nM.

Particularly the compounds of Examples 1-1, 1-2, 1-4 and 1-8 had values of $IC_{50}$ of 0.024, 0.038, 0.019 and 0.038, respectively, and had an excellent inhibitory effect on VR1 activity.

On the other hand, the values of $IC_{50}$ of the compounds of Comparative Examples 1 to 13 were, as shown in Tables 4 to 6, 3 nM, 1.3 nM, 18 nM, 5.2 nM, 42.0 nM, 0.3 nM, 0.4 nM, 7 nM, 0.12 nM, 0.04 nM, 0.36 nM, 0.03 nM and 0.12 nM, respectively, and the average value of $IC_{50}$ of these thirteen compounds of Comparative Examples was 5.99 nM.

As described above, the compound of the present invention had inhibitory activity about 24 times those of the compounds of Comparative Examples in terms of the average values of $IC_{50}$.

[2] Discussion about Result of Metabolic Stability Test in Human Liver S9 (Test Example [2]);

The human liver S9 remaining ratios of the compounds of Examples 1-1 to 1-10 included in the compound of the present invention represented by the general formula [1] were, as shown in Tables 4 to 6, 90.8%, 65.3%, 59.6%, 39.7%, 82.2%, 91.8%, 50.4%, 91.5%, 77.3% and 92.2%, respectively, and the average human liver S9 remaining ratio of these ten compounds was 74%.

Particularly the compounds of Examples 1-1, 1-6, 1-8 and 1-10 had 90% or higher remaining ratios and exhibited remarkably high remaining ratios, i.e., remarkably high metabolic stability in liver S9. Therefore, these compounds will be useful as drugs remarkably excellent in that they can resist oxidative metabolism and have the sustainability of the effect.

On the other hand, the human liver S9 remaining ratio of the compounds of Comparative Examples 1 to 13 were, as shown in Tables 4 to 6, 86.3%, 90.1%, 89.4%, 92.5%, 64.9%, 77.3%, 55.1%, 62.9%, 65.9%, 82.3%, 66.7%, 54.5% and 91.3%, respectively, and the average remaining ratio of these thirteen compounds of Comparative Examples was 75%.

[3] Discussion about Result of In-Vitro Membrane Permeability Test (Test Example [3]);

The in-vitro membrane permeability of the compounds of Examples 1-1 to 1-10 included in the compound of the present invention represented by the general formula [1] was, as shown in Tables 4 to 6, $8.59 \times 10^{-6}$, $20.96 \times 10^{-6}$, $26.93 \times 10^{-6}$, $30.25 \times 10^{-6}$, $38.07 \times 10^{-6}$, $37.53 \times 10^{-6}$, $37.94 \times 10^{-6}$, $13.61 \times 10^{-6}$, $50.36 \times 10^{-6}$ and $39.22 \times 10^{-6}$, respectively, in terms of the Papp values (cm/sec.), and the average Papp value (cm/sec.) of these ten compounds was $30.35 \times 10^{-6}$.

Particularly the compounds of Examples 1-2 to 1-10 had $10 \times 10^{-6}$ (cm/sec.) or more membrane permeability and exhibited remarkably high membrane permeability. Therefore, these compounds have exceedingly excellent properties as drugs because they have not only excellent values of $IC_{50}$ but also high absorbability which is a must for being practically used as a drug.

On the other hand, the Papp values (cm/sec.) of the compounds of Comparative Examples 1 to 13 were, as shown in Tables 4 to 6, $27.1 \times 10^{-6}$, $24.2 \times 10^{-6}$, $25.6 \times 10^{-6}$, $5.3 \times 10^{-6}$, $7.9 \times 10^{-6}$, $21.1 \times 10^{-6}$, $18.2 \times 10^{-6}$, $43.1 \times 10^{-6}$, $19.4 \times 10^{-6}$, $6.7 \times 10^{-6}$, $40.3 \times 10^{-6}$, $10.4 \times 10^{-6}$ and $28.6 \times 10^{-6}$, respectively, and the average Papp value (cm/sec.) of these thirteen compounds of Comparative Examples was $21.38 \times 10^{-6}$.

As described above, the compound of the present invention had membrane permeability about 1.4 times those of the compounds of Comparative Examples in terms of the average Papp values.

[4] Discussion about Result of Stability Test in Japanese Pharmacopoeia 1 Solution (Test Example [4]);

In the stability test in Japanese Pharmacopoeia 1 solution, the remaining ratios of the compounds of Examples 1-6 and 1-8 included in the compound of the present invention represented by the general formula [1] were 100 and 101%, respectively. On the other hand, the remaining ratio of the compound of Comparative Example 13 was 62.1%.

Since it is assumed that the Japanese Pharmacopoeia 1 solution has pH equal to that of gastric acid, it is generally known that stability therein suggests stability in gastric juice.

Therefore, these compounds, as compared with the compound of Comparative Example 13, will be useful as drugs excellent in that they can be stable in gastric juice.

[5] Summary;

(1) Regarding Value of $IC_{50}$;

According to the document (J Pharmacol Exp Ther. 2003 July; 306 (1): 377-86), it is known that BCTC, which is known as a substance inhibiting VR1 activity, has its inhibitory activity (value of $IC_{50}$) of several nM. Moreover, we have also confirmed in our tests that the value of $IC_{50}$ of BCTC is several nM.

All the values of $IC_{50}$ of the compound of the present invention, specifically the compounds of the present Examples 1-1 to 1-10 are less than 1 nM.

On the other hand, of the compounds of Comparative Examples, seven compounds of Comparative Examples 6, 7, 9, 10, 11, 12 and 13 had values of $IC_{50}$ less than 1 nM. However, these seven compounds of Comparative Examples were not necessarily satisfiable with all things considered, for such reasons as they had remaining ratios less than 80% in the metabolic stability test in liver S9 and/or Papp values less than $10 \times 10^{-6}$ corresponding to membrane permeability or had inferior stability in gastric juice.

(2) Regarding Metabolic Stability in Human Liver S9;

Metabolic stability is one of important requirements for a drug, and those having 80% or higher metabolic stability are preferred. The compounds of Examples 1-1, 1-6, 1-8 and 1-10 had 90% or higher remaining ratios and exhibited remarkably high remaining ratios, i.e., remarkably high metabolic stability in liver S9.

On the other hand, the compounds of Comparative Examples 1, 2, 3, 4, 10, 13, etc. also exhibited excellent metabolic stability. However, the compounds of Comparative Examples 1, 2, 3 and 4 had values of $IC_{50}$ of 1 nM or higher and were not satisfiable in light of inhibitory activity. The compound of Comparative Example 10 had a Papp value of $6.7 \times 10^{-6}$ and was not satisfiable in light of membrane permeability. Moreover, the compound of Comparative Example 13 had inferior stability in gastric juice and was not necessarily satisfiable.

(3) Regarding Result of Membrane Permeability Test;

Regarding membrane permeability, the compound of the present invention had membrane permeability about 1.4 times those of the compounds of Comparative Examples in terms of the average Papp values, as described above. Particularly the compounds of Examples 1-4, 1-5, 1-6, 1-7, 1-9 and 1-10 had high membrane permeability of $30 \times 10^{-6}$ or more in terms of the Papp values.

On the other hand, of the compounds of Comparative Examples, the compounds of Comparative Examples 8 and 11 had high membrane permeability. However, the compound of Comparative Example 8 had a value of $IC_{50}$ of 7 nM corresponding to inhibitory activity and was not satisfiable in light of inhibitory activity. Moreover, the compound of Comparative Example 11 had a human liver S9 remaining ratio of 66.7% serving as an index of metabolic stability and was not necessarily satisfiable as a drug.

(4) Characteristics of Compound of the Present Invention from the Viewpoint of Chemical Structure;

When the compound of Comparative Example 11 and the compound of Example 1-2 are compared, they are different in that the former has only one fluorine atom in the phenyl group whereas the latter has two fluorine atoms. The latter has the value of $IC_{50}$ about 10 times higher than that of the former.

When the compound of Comparative Example 8 and the compound of Example 1-6 are compared, they are different only in that the former has a trifluoromethyl group as a substituent for pyridine whereas the latter has a 2,2,2-trifluoroethoxy group. The latter is improved in its liver S9 remaining ratio which is about 1.5 times that of the former and in its value of $IC_{50}$ which is about 50 times that of the former.

When the compounds of Comparative Examples 7 and 9 and the compound of Example 1-8 are compared, the compound of Example 1-8 which has two fluorine atoms and one 2,2,2-trifluoroethoxy group as substituents for a phenyl group is different from the others in that the compound of Comparative Example 7 has only one trifluoromethyl group and in that the compound of Comparative Example 9 merely has one fluorine atom and one trifluoromethyl group. However, the compound of Example 1-8 is improved in its liver S9 remaining ratio which is about 1.4 to 1.7 times those of the compounds of Comparative Examples 7 and 9 and in its value of $IC_{50}$ which is about 3 to 11 times those of the compounds of Comparative Examples 7 and 9.

When the compound of Comparative Example 13 and the compound of Example 1-1 are compared, they are different in that the former has only one fluorine atom in the phenyl group whereas the latter has two fluorine atoms. The latter has the value of $IC_{50}$ about 5 times higher than that of the former. This was a result which was not expectable even by those skilled in the art.

The compound represented by the general formula [1], particularly the compounds of Examples 1-1 to 1-10 are compounds having excellent inhibitory activity on VR1 as well as excellent metabolic stability in liver S9 and/or high membrane permeability.

Therefore, the compounds of Examples 1-1 to 1-10 included in the compound represented by the general formula [1] not only are useful as drugs remarkably excellent in effectiveness as VR1 activity inhibitors but also will be useful as drugs remarkably excellent in that they can resist oxidative metabolism and have the sustainability of the effect as well as in that they can have high absorbability.

Therefore, these compounds not only are useful as drugs remarkably excellent in effectiveness as VR1 activity inhibitors but also are expected to be practically used as drugs remarkably excellent in that they can resist oxidative metabolism and have the sustainability of the effect as well as in that they can have high absorbability.

INDUSTRIAL APPLICABILITY

The 3,4-dihydrobenzoxazine compound of the present invention effectively inhibits vanilloid receptor subtype 1 (VR1) activity, and therefore it is effective in the medical treatment and/or prevention of diseases such as pain, acute pain, chronic pain, neuropathic pain, rheumatoid arthritis pain, neuralgia, neuropathy, hyperalgesia, migraine, joint pain, acute herpetic pain, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, overactive bladder type frequent urination, and overactive bladder type urinary incontinence.

The invention claimed is:

1. A 3,4-dihydrobenzoxazine compound selected from the following group or a pharmaceutically acceptable salt thereof:
   1) (S)-4-(5-picolin-2-yl)-3-hydroxymethyl-N-(4-tert-butoxy-3,5-difluorophenyl)-3,4-dihydro-2H-benzo[1,4]oxazine-8-carboxamide,
   2) (S)-4-(5-picolin-2-yl)-3-hydroxymethyl-N-(3,5-difluoro-4-isopropoxyphenyl)-3,4-dihydro-2H-benzo[1,4]oxazine-8-carboxamide,
   3) (S)-4-(5-picolin-2-yl)-3-hydroxymethyl-N-(3,5-difluoro-4-ethoxyphenyl)-3,4-dihydro-2H-benzo[1,4]oxazine-8-carboxamide,
   4) (S)-4-(5-picolin-2-yl)-3-hydroxymethyl-N-[2-(2,2-dimethylpropyloxy)pyridin-5-yl]-3,4-dihydro-2H-benzo[1,4]oxazine-8-carboxamide,
   5) (S)-4-(5-picolin-2-yl)-3-hydroxymethyl-N-(2-tert-butoxypyridin-5-yl)-3,4-dihydro-2H-benzo[1,4]oxazine-8-carboxamide,
   6) (S)-4-(5-picolin-2-yl)-3-hydroxymethyl-N-[2-(2,2,2-trifluoroethyloxy)pyridin-5-yl]-3,4-dihydro-2H-benzo[1,4]oxazine-8-carboxamide,
   7) (S)-4-(5-picolin-2-yl)-3-hydroxymethyl-N-(2-isobutoxypyridin-5-yl)-3,4-dihydro-2H-benzo[1,4]oxazine-8-carboxamide,
   8) (S)-4-(5-picolin-2-yl)-3-hydroxymethyl-N-[3,5-difluoro-4-(2,2,2-trifluoroethoxy)phenyl]-3,4-dihydro-2H-benzo[1,4]oxazine-8-carboxamide,
   9) (S)-4-(5-picolin-2-yl)-3-hydroxymethyl-N-[3,5-difluoro-4-(2-hydroxy-2-methylpropyloxy)phenyl]-3,4-dihydro-2H-benzo[1,4]oxazine-8-carboxamide, and
   10) (S)-4-(5-picolin-2-yl)-3-hydroxymethyl-N-[3,5-difluoro-4-(1,1-dimethyl-2-hydroxyethyloxy)phenyl]-3,4-dihydro-2H-benzo[1,4]oxazine-8-carboxamide.

2. A pharmaceutical composition comprising (a) a 3,4-dihydrobenzoxazine compound or a pharmaceutically acceptable salt thereof according to claim 1 and (b) a pharmaceutically acceptable carrier.

3. A pharmaceutical composition comprising (a) a 3,4-dihydrobenzoxazine compound or a pharmaceutically acceptable salt thereof according to claim 1, (b) a pharmaceutically acceptable carrier, and (c) one or more agents selected from the group consisting of an anti-virus agent, an antidepressant, an anticonvulsant, an antiarrhythmic, a local anesthetic, an anesthetic, an N-methyl-D-aspartate receptor antagonist, an adrenal cortical steroid, a nerve block, a nonsteroidal antiinflammatory analgesic, a narcotic, an antagonist analgesic, an $\alpha_2$-adrenaline receptor agonist, a medicine for external application, a calcium channel antagonist, a potassium channel opener, and an antipyretic agent.

4. A method for treating a disease of an animal, wherein the method comprises administering a pharmacologically effective amount of a 3,4-dihydrobenzoxazine compound or a pharmaceutically acceptable salt thereof according to claim 1 to an animal with a disease selected from the group consisting of pain, acute pain, chronic pain, neuropathic pain, rheumatoid arthritis pain, neuralgia, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, cerebral apoplexy, ischemic symptom, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence, whereby the disease of the animal is treated.

5. A method for treating pain of an animal, wherein the method comprises administering a pharmacologically effective amount of a 3,4-dihydrobenzoxazine compound or a pharmaceutically acceptable salt thereof according to claim 1 to an animal with pain, whereby the pain of the animal is treated.

6. The method of claim 5, wherein the pain is selected from the group consisting of acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, and neurodegenerative disease.

7. A method for treating a disease of an animal, wherein the method comprises (a) administering one or more agents selected from the group consisting of an anti-virus agent, an antidepressant, an anticonvulsant, an antiarrhythmic drug, a local anesthetic, an anesthetic drug, an N-methyl-D-aspartate receptor antagonist, adrenal cortical steroid, a nerve block, a nonsteroidal antiinflammatory analgesic, narcotics, an antagonist analgesic, $\alpha_2$-adrenaline receptor agonist, a medicine for external application, a calcium channel antagonist, a potassium channel opener, and an antipyretic agent to an animal in combination with (b) administering a pharmacologically effective amount of a 3,4-dihydrobenzoxazine compound or a pharmaceutically acceptable salt thereof according to claim 1 to the animal with a disease selected from the group consisting of pain, acute pain, chronic pain, neuropathic pain, rheumatoid arthritis pain, neuralgia, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, cerebral apoplexy, ischemic symptom, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence, whereby the disease of the animal is treated.

8. A method for treating pain of an animal, wherein the method comprises administration of a 3,4-dihydrobenzoxazine compound or a pharmaceutically acceptable salt thereof according to claim 2 to an animal with pain in combination with effecting stimulation-produced analgesia by subjecting the animal to one or more of the therapies selected from the group consisting of acupuncture, transcutaneous electroacupuncture stimulation therapy, transcutaneous electrical nerve stimulation therapy, silver spike point (SSP) therapy, peripheral nerve stimulation therapy, spinal cord electrical stimulation therapy, electroconvulsive therapy, laser therapy and low-frequency therapy, whereby the pain of the animal is treated.

9. A method for treating postoperative neuralgia in an animal, wherein the method comprises administrating a 3,4-dihydrobenzoxazine compound or a pharmaceutically acceptable salt thereof according to claim 1 to an animal after performing a surgical operation selected from the group consisting of cicatrectomy, nerve freezing solidification, peripheral nerve excision, spinal cord dorsal root excision, sympathectomy, spinal cord dorsal root entry zone destruction, cordotomy, and frontal lobe excision on the animal, whereby postoperative neuralgia in the animal is treated.

10. The method of any one of claim 4, 5, 6, 7, 8, or 9, wherein the animal is human.

11. The 3,4-dihydrobenzoxazine compound of claim 1 represented by the following formula or a pharmaceutically acceptable salt thereof:

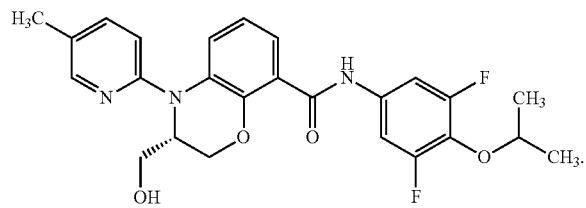

12. The 3,4-dihydrobenzoxazine compound of claim 1 represented by the following formula or a pharmaceutically acceptable salt thereof:

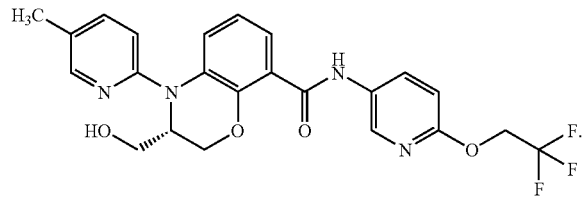

13. The 3,4-dihydrobenzoxazine compound of claim 1 represented by the following formula or a pharmaceutically acceptable salt thereof:

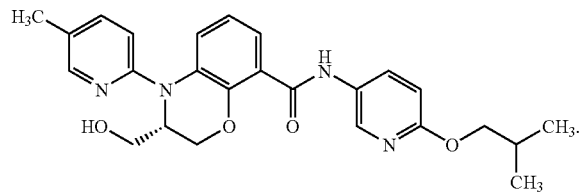

14. The 3,4-dihydrobenzoxazine compound of claim 1 represented by the following formula or a pharmaceutically acceptable salt thereof:

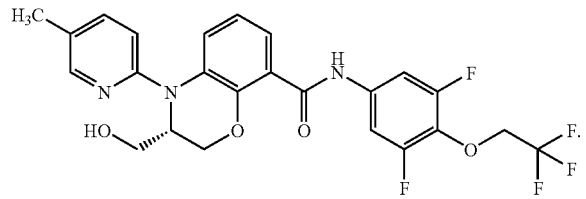

15. The 3,4-dihydrobenzoxazine compound of claim 1 represented by the following formula or a pharmaceutically acceptable salt thereof:

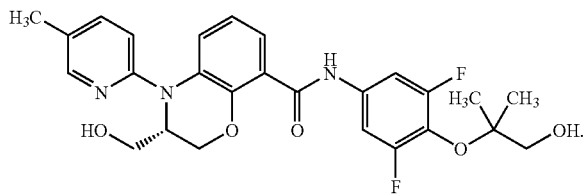

16. A pharmaceutical composition comprising (a) a 3,4-dihydrobenzoxazine compound or a pharmaceutically acceptable salt thereof according to any one of claims 11-15 and (b) a pharmaceutically acceptable carrier.

17. A method for treating a disease of an animal, wherein the method comprises administering a pharmacologically effective amount of a 3,4-dihydrobenzoxazine compound or a pharmaceutically acceptable salt thereof according to any one of claims 11-15 to an animal with a disease selected from the group consisting of pain, acute pain, chronic pain, neuropathic pain, rheumatoid arthritis pain, neuralgia, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, cerebral apoplexy, ischemic symptom, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence, whereby the disease of the animal is treated.

18. A method for treating pain of an animal, wherein the method comprises administering a pharmacologically effective amount of a 3,4-dihydrobenzoxazine compound or a pharmaceutically acceptable salt thereof according to any one of claims 11-15 to an animal with pain, whereby the pain of the animal is treated.

19. A method for treating a disease of an animal, wherein the method comprises (a) administering one or more agents selected from the group consisting of an anti-virus agent, an antidepressant, an anticonvulsant, an antiarrhythmic drug, a local anesthetic, an anesthetic drug, an N-methyl-D-aspartate receptor antagonist, adrenal cortical steroid, a nerve block, a nonsteroidal antiinflammatory analgesic, narcotics, an antagonist analgesic, $α_2$-adrenaline receptor agonist, a medicine for external application, a calcium channel antagonist, a potassium channel opener, and an antipyretic agent to an animal in combination with (b) administering a pharmacologically effective amount of a 3,4-dihydrobenzoxazine compound or a pharmaceutically acceptable salt thereof according to any one of claims 11-15 to the animal with a disease selected from the group consisting of pain, acute pain, chronic pain, neuropathic pain, rheumatoid arthritis pain, neuralgia, hyperalgesia, migraine, joint pain, acute post herpetic neuralgia, postherpetic neuralgia, chronic postherpetic neuralgia, postoperative pain, cancer pain, inflammatory pain, interstitial cystitis, posttraumatic neuralgia, diabetic neuropathy, cerebral apoplexy, ischemic symptom, pruritus, allergic rhinitis, apoplexy, irritable bowel syndrome, asthma, chronic obstructive pulmonary disease, dermatitis, mucositis, stomach and duodenal ulcer, inflammatory bowel disease, bladder hypersensitivity, frequent urination, and urinary incontinence, whereby the disease of the animal is treated.

20. A method for treating pain of an animal, wherein the method comprises administration of a 3,4-dihydrobenzoxazine compound or a pharmaceutically acceptable salt thereof according to any one of claims 11-15 to an animal with pain in combination with effecting stimulation-produced analgesia by subjecting the animal to one or more of the therapies selected from the group consisting of acupuncture, transcutaneous electroacupuncture stimulation therapy, transcutaneous electrical nerve stimulation therapy, silver spike point (SSP) therapy, peripheral nerve stimulation therapy, spinal cord electrical stimulation therapy, electroconvulsive therapy, laser therapy and low-frequency therapy, whereby the pain of the animal is treated.

21. A method for treating postoperative neuralgia in an animal, wherein the method comprises administrating a 3,4-dihydrobenzoxazine compound or a pharmaceutically acceptable salt thereof according to any one of claims 11-15 to an animal after performing a surgical operation selected from the group consisting of cicatrectomy, nerve freezing solidification, peripheral nerve excision, spinal cord dorsal root excision, sympathectomy, spinal cord dorsal root entry zone destruction, cordotomy, and frontal lobe excision on the animal, whereby postoperative neuralgia in the animal is treated.

* * * * *